United States Patent
Liang et al.

(10) Patent No.: US 9,678,037 B2
(45) Date of Patent: Jun. 13, 2017

(54) TWO-DIMENSIONAL MATERIAL-BASED FIELD-EFFECT TRANSISTOR SENSORS

(71) Applicant: THE REGENTS OF THE UNIVERSITY OF MICHIGAN, Ann Arbor, MI (US)

(72) Inventors: Xiaogan Liang, Ann Arbor, MI (US); Katsuo Kurabayashi, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 0 days.

(21) Appl. No.: 14/878,616

(22) Filed: Oct. 8, 2015

(65) Prior Publication Data
US 2017/0102357 A1    Apr. 13, 2017

(51) Int. Cl.
*G01N 15/06* (2006.01)
*G01N 33/00* (2006.01)
*G01N 33/48* (2006.01)
*G01N 27/414* (2006.01)
(Continued)

(52) U.S. Cl.
CPC ..... *G01N 27/4146* (2013.01); *G01N 33/6863* (2013.01); *H01L 29/7781* (2013.01); *G01N 2333/525* (2013.01)

(58) Field of Classification Search
CPC ......... G01N 15/06; G01N 33/00; G01N 33/48
USPC .... 422/68.1, 82.01, 502, 503; 257/253, 262, 257/133, 205, 213, 252; 435/287.2, 435/287.8, 287.9, 286.5
See application file for complete search history.

(56) References Cited

U.S. PATENT DOCUMENTS 8,981,345 B2 * 3/2015 Yu et al. .......................... 257/29
9,076,686 B1 * 7/2015 Karda et al.
9,178,032 B2 * 11/2015 Yu et al.
(Continued)

FOREIGN PATENT DOCUMENTS

| EP | 2304420 A2 | 4/2011 |
| KR | 20100100083 A | 9/2010 |
| WO | WO-2014146020 A2 | 9/2014 |

OTHER PUBLICATIONS

H. Nam et al "Two different device physics principles for operating MoS transistor biosensors with femtomolar-level detection limits" (2015) Applied Physics Letter 107, 012105.
(Continued)

*Primary Examiner* — Brian J Sines
(74) *Attorney, Agent, or Firm* — Harness, Dickey & Pierce, PLC

(57) ABSTRACT

Atomically layered transition metal dichalcogenides (TM-DCs) exhibit a significant potential to enable low-cost transistor biosensors that permit single-molecule-level quantification of biomolecules. Two different principles for operating such biosensors are presented. In one arrangement, antibody receptors are functionalized on an insulating layer deposited onto the channel of the transistor. The charge introduced through antigen-antibody binding is capacitively coupled with the channel and shifts the threshold voltage without significantly changing the transconductance. In another arrangement, antibodies are functionalized directly on the channel of the transistor. Antigen-antibody binding events mainly modulate the ON-state transconductance, which is attributed to the disordered potential formed in channel material.

15 Claims, 18 Drawing Sheets

(51) Int. Cl.
*H01L 29/778* (2006.01)
*G01N 33/68* (2006.01)

(56) References Cited

U.S. PATENT DOCUMENTS

2004/0007740 A1* 1/2004 Abstreiter et al. ............ 257/347
2013/0307029 A1* 11/2013 Xu et al. ....................... 257/253

OTHER PUBLICATIONS

H. Nam et al Multiple $MoS_2$ Transistors for Sensing Molecule interaction Kinetics, (2015) Scientific Reports, 5, 10546.

* cited by examiner

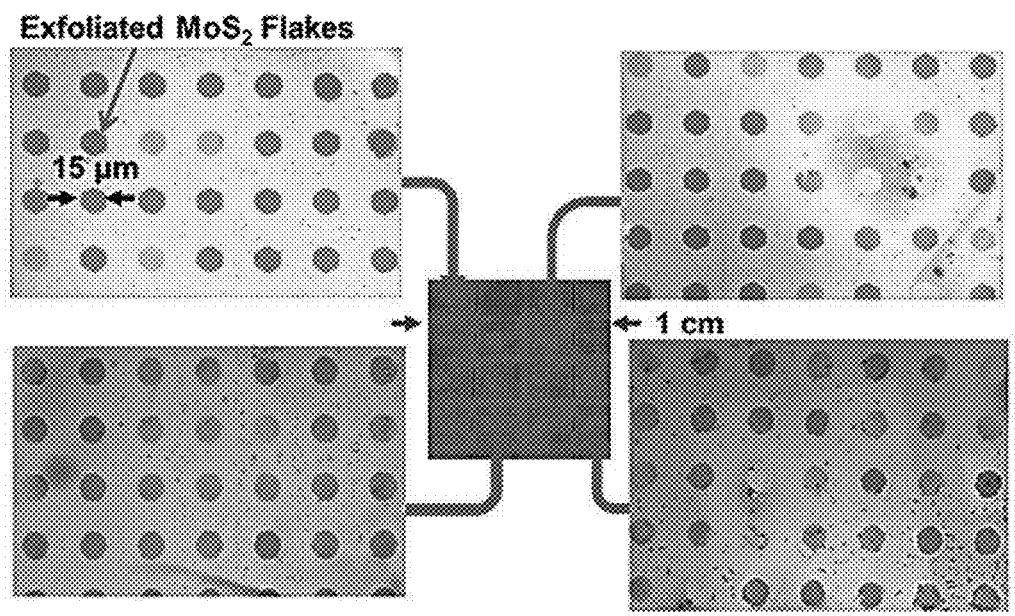
FIG. 13A
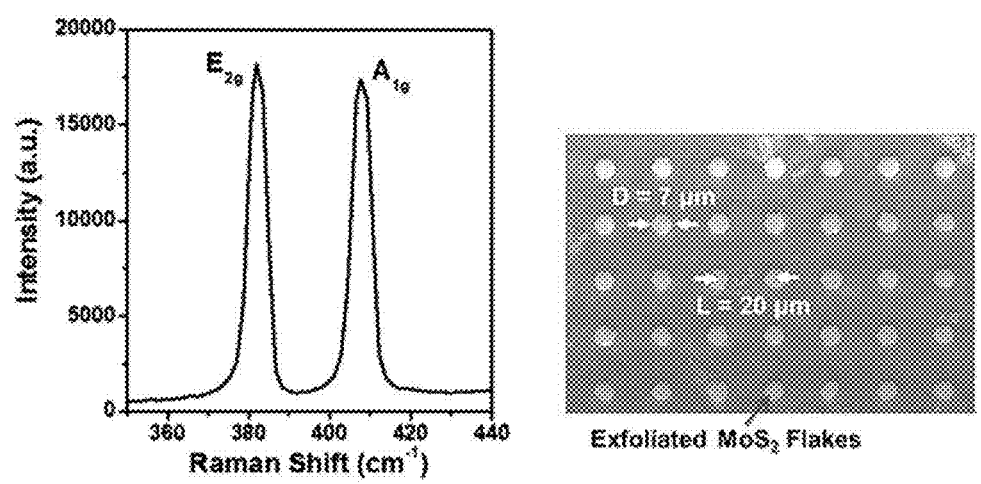
FIG. 13B
FIG. 13C

TWO-DIMENSIONAL MATERIAL-BASED FIELD-EFFECT TRANSISTOR SENSORS

GOVERNMENT CLAUSE

This invention was made with government support under ECCS1452916 awarded by the National Science Foundation. The Government has certain rights in the invention.

FIELD

The present disclosure relates to biosensors and, more particularly, a sensor arrangement using a field-effect transistor having an atomically thin channel structure.

BACKGROUND

Using field-effect transistor (FET)-based biosensors created from nanowires (NWs) and carbon nanotubes (CNTs), researchers have demonstrated detection of cancer biomarkers from nM to fM range in serum, in vitro detection of nM proteins in cell growth systems, and quanitification of the affinities/kinetics of the protein interactions with fM-level sensitivities. The fM-level limit-of-detection (LOD) achieved by such nanoscale FET biosensors for monitoring biomarker concentrations would enable label-free, single-molecule-level detection of trace-level amount biomarkers. The arrays of such biosensors with consistent transistor responses would serve as reliable lab-on-a-chip platforms for precisely determining the kinetics of various biomolecule interactions. However, serious constraints imposed on nanofabrication severely prohibit the reliable manufacturing of the affordable biosensor chips utilizing such one dimensional (1D) nanostructures. In particular, high-quality, small-size NWs and CNTs are needed to make biosensors with fM-level LOD for concentration monitoring (or single-molecule-level LOD for trace-level amount detection). Especially, for trace-level amount detection, the critical dimensions of the sensing channels need to be comparable to the impact dimensions of charged molecules to maximize the gating effect due to the charged molecules and achieve very low LOD. CNTs and many NWs are usually produced by using bottom-up synthesis methods (e.g., chemical, vapor deposition CVD)). The community currently lacks proper top-down planar nanofabrication processes to produce ordered arrays of such nanostructures, which makes it very challenging to realize parallel high-throughput assay using biosensors made from these nanostructures. High-quality Si NW biosensor arrays can be made using top-down lithographic techniques. However, the fabrication of such Si NW arrays usually needs expensive semiconductor-on-insulator (SOI) substrates and exquisite nanolithographic tools, which can result in a high processing cost and is not very suitable for manufacturing affordable (even disposable) assay chips for practical clinical biosensing applications.

Emerging two-dimensional (2D) atomically layered materials, such as graphene, topological insulators (Tis), and transition metal dichalcogenides (TMDCs), recently attracted a great deal of interest because of their attractive electronic/optoelectronic properties, large abundance, and compatibility to planar nanofabrication processes. Due to their atomically thin structures, the transport properties of 2D layers are highly sensitive to the external stimuli, which can enable new ultrasensitive 2D FETs suitable for biosensing applications. Especially, in comparison with the thin film transistors made from conventional bulk semiconductors (e.g., Si and III-V compounds), the transistors based on molybdenum disulfide ($MoS_2$) and other atomically layered semiconductors are expected to exhibit much more sensitive electrical responses to antigen-antibody binding events. Furthermore, all 2D layers have an extremely low density of dangling bonds on their surfaces, which can result in high-quality FET channels with low densities of scattering centers (and hence low Flicker noise level), and enable highly sensitive, low-noise level detecting of biomolecules.

In contrast to zero-bandgap graphene, semiconducting TMDCs have sizable bandgaps. Therefore, TMDC-based FETs exhibit high On/Off current ratios up to $10^8$, which, in combination with their atomically thin structures, can potentially enable the higher detection sensitivities for gas, chemical, and biological sensing applications. Therefore, it is very promising to realize cost-efficient manufacturing of multiplexing assays based on TMDC transistor arrays in the future.

Toward such envisaged bio-assay capability, additional device-oriented research is needed for quantitatively calibrating the sensor responses measured from multiple sets of TMDC FET biosensors, so that the calibrated response signals are consistent with each other and can synergistically enable precise quantification of biomarker concentrations (or amounts) as well as the affinities/kinetics of biomolecule interactions.

This section provides background information related to the present disclosure which is not necessarily prior art.

SUMMARY

This section provides a general summary of the disclosure, and is not a comprehensive disclosure of its full scope or all of its features.

Two different principles are presented for operating a biosensor comprised of a transistor. In one arrangement, the biosensor includes: a field effect transistor (FET) formed on a substrate, where the FET includes a channel comprised of a monolayer of transition metal dichalcogenides; an insulating layer deposited onto the FET; an antibody functionalized onto the portion of the insulating layer which is deposited directly onto the channel; and a reservoir layer integrated on top of the FET, where the reservoir layer defines a fluidic channel having an inlet and an outlet and the fluidic channel runs along the portion of the insulating layer which is deposited directly onto the channel.

In another arrangement, the biosensor includes: a field effect transistor (FET) formed on the substrate, where the FET includes a channel comprised of a monolayer of transition metal dichalcogenides; an antibody functionalized onto an exposed surface of the channel of the FET; and a reservoir layer integrated on top of the FET, where the reservoir layer defines a fluidic channel having an inlet and an outlet and the fluidic channel runs along the exposed surface of the channel.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 13A is four optical micrographs of $MoS_2$ flake arrays imprinted/exfoliated into a PS fixing layer coated on a substrate using NASE, which were captured from different locations over the whole NASE-processed area (~1 cm2), as mapped in the inset of the whole NASE sample;

FIG. 13B is a Raman spectrum of an exemplary multilayer $MoS_2$ flake;

FIG. 13C-13E are SEM images of a set of NASE-produced arrays of multilayer $MoS_2$ flakes;

Figure 14A:
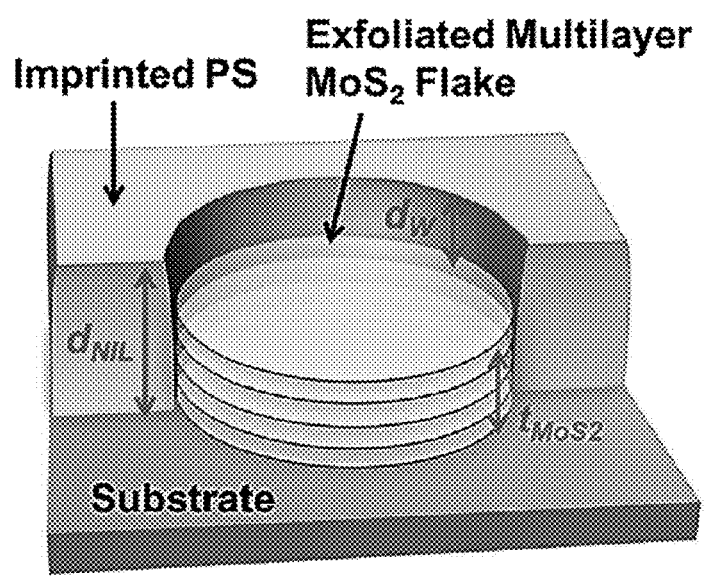
FIG. 14A is a schematic of a multilayer $MoS_2$ flake with thickness of $MoS_2$ exfoliated into an imprinted PS well with imprint depth of $d_{NIL}$, resulting in an effective well depth of $d_w$.
Figure 14B:
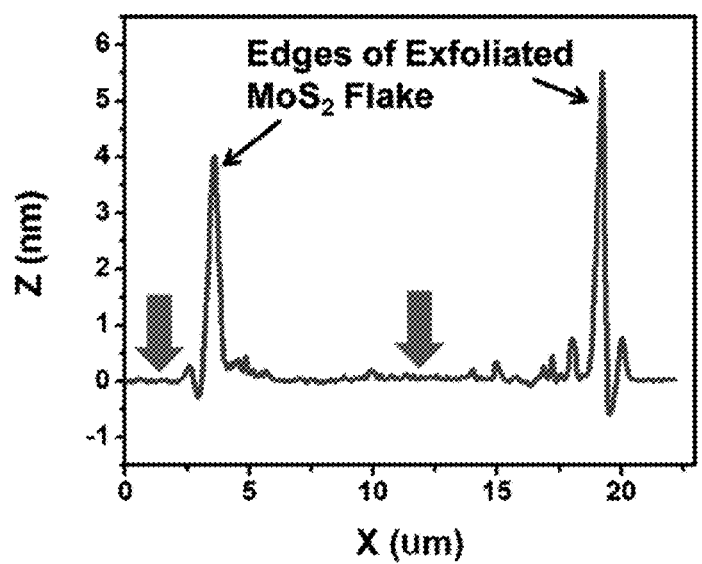
FIG. 14B is a graph of an AFM scanline extracted from an AFM image.
Figure 14C:
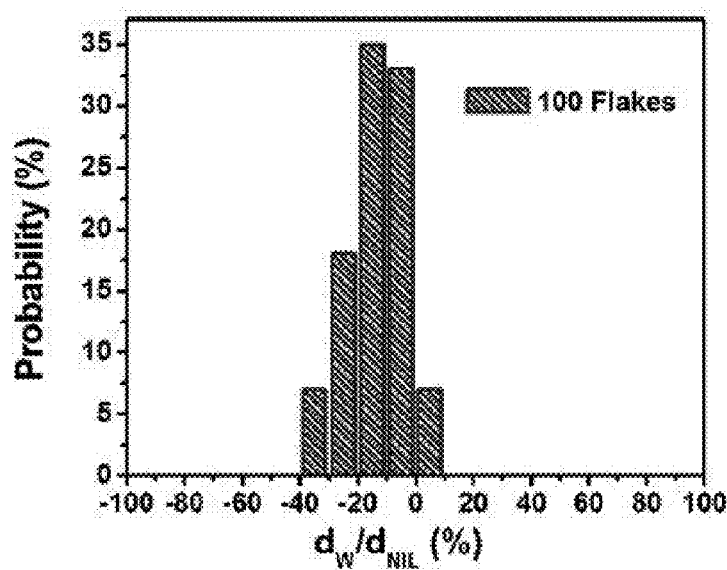
Figure 15A:
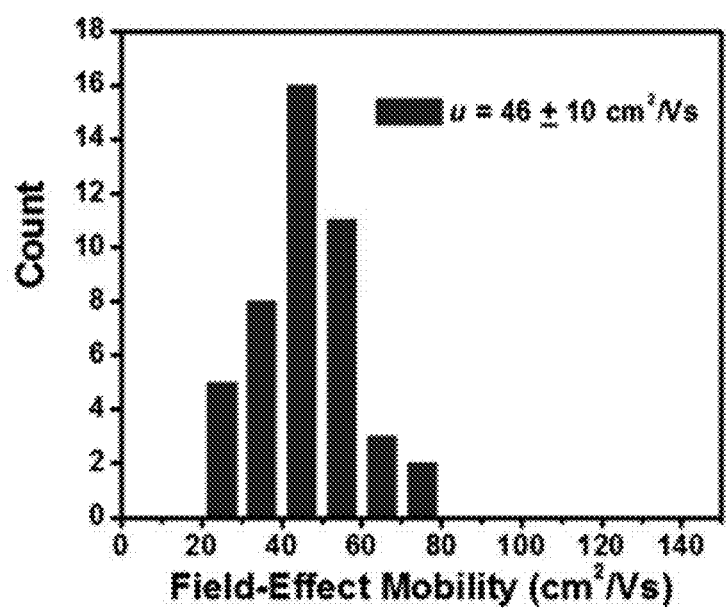
Figure 15B:
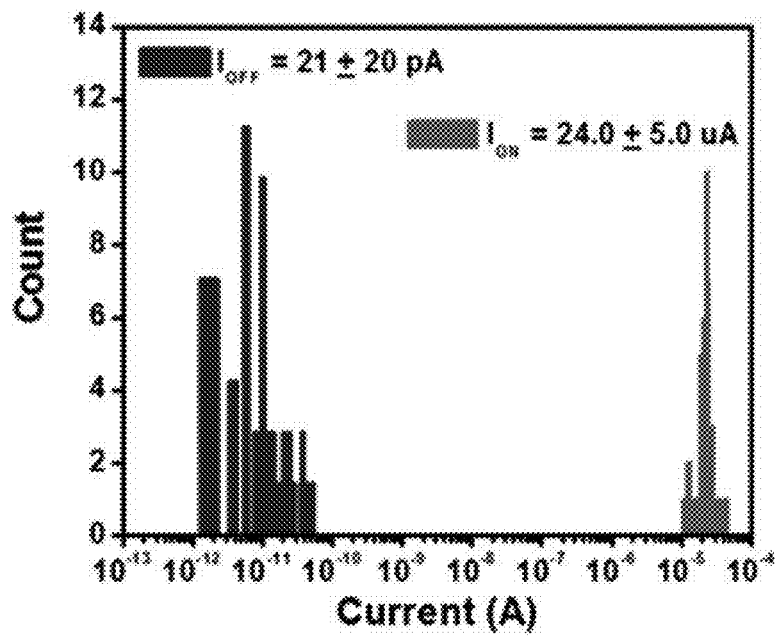
Figure 15C:
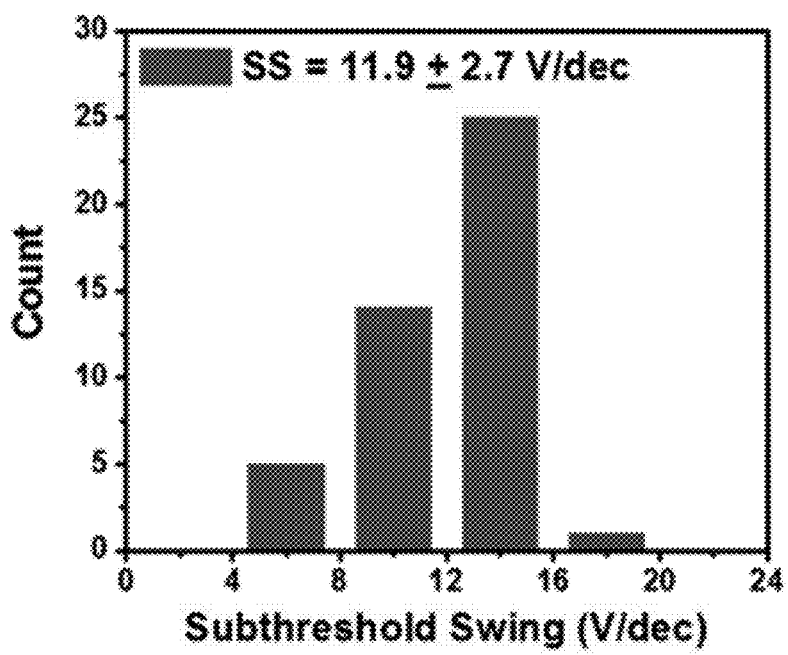
Figure 15D:
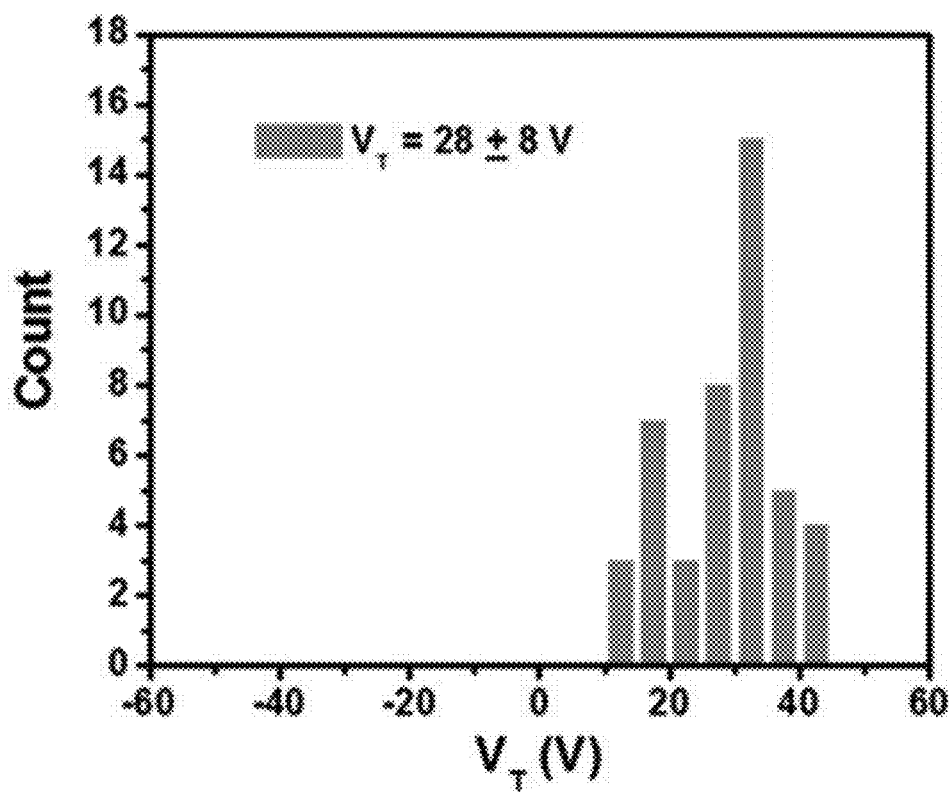

FIG. 14C is a graph depicting statistics of $d_w/d_{NIL}$ data measured from 100 $MoS_2$-embeded wells, which shows that the standard deviation of $d_w/d_{NIL}$ data (or the relative thickness error of NASE-produced multilayer MoS2 flakes) is estimated to ~12%; and FIGS. 15A-15D are graphs showing the statistics of mobility (φ, On/Off currents (ION and IOFF), subthreshold swing (SS), and threshold voltage (VT) data, respectively, as measured from 45 $MoS_2$ FETs fabricated by a NASE process.

Corresponding reference numerals indicate corresponding parts throughout the several views of the drawings.

DETAILED DESCRIPTION

Example embodiments will now be described more fully with reference to the accompanying drawings.

Figure 1:
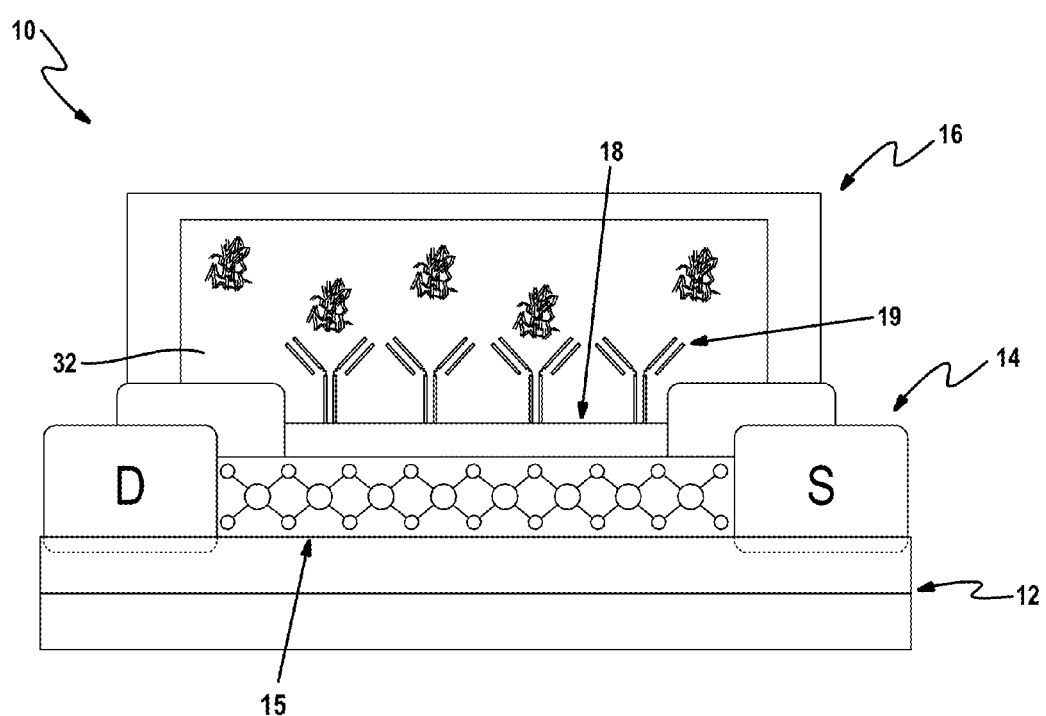
FIG. 1 is a cross-sectional view of an example embodiment of a biosensor.

FIG. 1 depicts an example embodiment of a biosensor 10 which employs an atomically thin channel structure. The biosensor is comprised generally of a field effect transistor (FET) 14 formed on a substrate 12 and a reservoir layer 16 integrated on top of the FET 14. An insulating layer 18 may be deposited on the FET 14, where at least a portion of the insulating layer 18 is deposited directly onto the channel region 15 of the FET 14. In one embodiment, the insulating layer 18 covers only the exposed surface of the channel of the FET 14. During sensing, an antibody 19 is functionalized onto the portion of the insulating layer 18 which is deposited onto the channel region of the FET 14. While reference is made throughout this disclosure to a field effect transistor, other types of transistors fall within the broader aspects of this disclosure.

Figure 2A:
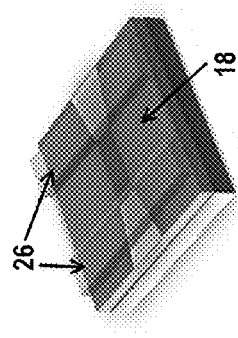
FIGS. 2A-2E are diagrams illustrating the fabrication of the biosensor.

FIGS. 2A-2E further illustrate the steps for fabricating the biosensor 10. First, a channel region 21 for the FET 14 is formed onto the substrate 12 as seen in FIG. 2A. In the example embodiment, the channel region 21 is formed from a monolayer of transition metal dichalcogenides material, such as molybdenum disulfide or tungsten diselenide. More specifically, a pristine few-layer $MoS_2$ flake is printed onto the substrate, where the substrate is formed by a p+-doped silicon (Si) 23 coated with 300 nm thick $SiO_2$ 22. The thickness of the flake chosen for making a biosensor is specifically controlled to be 15-20 nm, aiming to achieve relatively high field-effect mobility values (μ=20 to 30 cm$^2$/Vs). The transistor channel lengths (L) were ~5 μm and the channel widths (W) ranged from 5 to 8 μm. Other types of two-dimensional nanomaterials also fall within the scope of this disclosure.

Figure 2B:
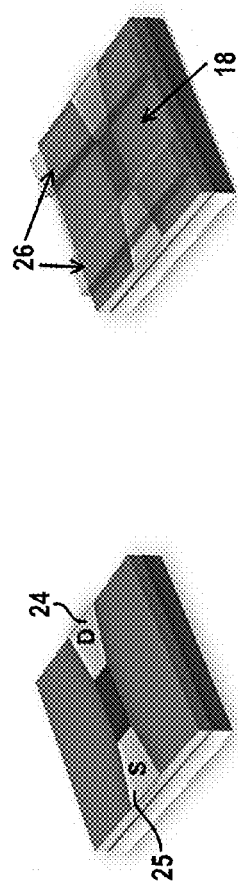

After forming the channel region, drain and source contacts 24, 25 are fabricated, for example using photolithography followed with metal deposition and lift-off as seen in FIG. 2B. In the example embodiment, Ti (e.g., 5 nm)/Au (e.g., 50 nm) electrode pairs serve as drain (D) and source (S) contacts 24, 25 although other metals are contemplated by this disclosure. The p+-Si substrates were used as the back gates (G). Thermally grown SiO2 layers (300 nm thick) were used as the back-gate dielectrics.

Figure 2C:
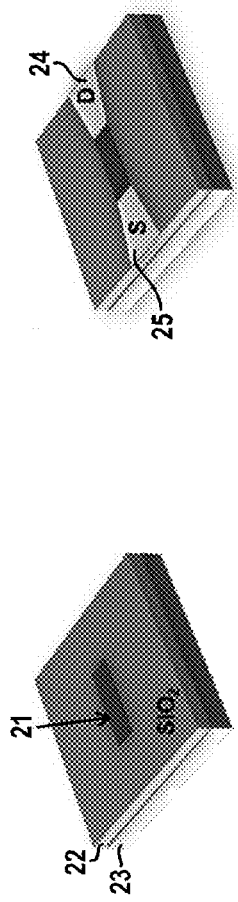

To enable a capacitive coupling between the microfluidic reservoir and the channel region of the FET 14, the insulating layer 18 is deposited on the FET 14 as seen in FIG. 2C. In the example embodiment, a 30 nm thick $HfO_2$ layer is deposited on top of the $MoS_2$ channel, for example using atomic layer deposition (ALD). This $HfO_2$ layer also serves as an effective layer for biofunctionalization. Afterwards, additional insulating layer (e.g., 100 nm thick $SiO_x$) is sputtered onto the drain and source contacts 24, 25 to minimize the leakage current between the contacts and microfluidic components. Different types of insulating materials are contemplated by this disclosure.

Before the TNF-α detection, anti-human TNF-α antibody is functionalized on the HfO$_2$ effective layer. First, the as-fabricated biosensor 10 is immersed in 5% (3-Aminopropyl) triethoxysilane (APTES) in ethanol for one hour. After the incubation, the sensor is rinsed with phosphate buffered saline (PBS) and blown dry by nitrogen gas. After this step, the HfO$_2$ effective layer is silanized with an APTES monolayer. The device is subsequently immersed in 5% gluteraldelhyde (GA) in PBS for two hours followed by rinsing with PBS. Afterwards, anti-human TNF-α antibody of 50 ug/ml concentration in deionized (DI) water is dropped on the sensor and incubated for one hour. This technique is merely exemplary and other techniques for functionalizing an antibody on the insulating layer also fall within the scope of this disclosure.

Figure 2D:
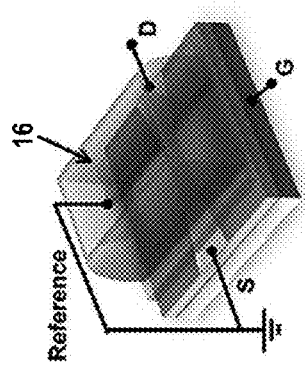
Figure 2E:
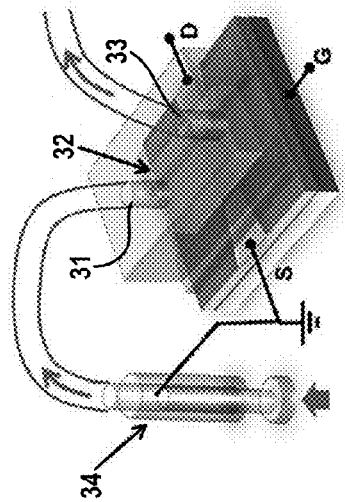

To measure sensor responses from different TNF-α concentrations under the thermodynamic equilibrium condition and determine the affinity of the antibody-(TNF-α) pair, a large open liquid reservoir 16 is formed on top of the FET 14. Referring to FIG. 2D, the reservoir layer 16 defines a fluidic channel having an inlet 31 and an outlet 33 and a passageway 32 extending between the inlet and the outlet, such that the passageway 32 runs along the exposed surface of the insulating layer 18. In the example embodiment, the reservoir is ~4 mm deep and is ~1 mm in diameter, and includes a fluidic channel with length, width, and thickness of 2, 1 and 0.4 cm, respectively. The reservoir layer 16 may be formed from polydimethysiloxane (PDMS) or other silicone materials. A pump 34 can be used for driving the TNF-α solution flow into and out of the microfluidic channel using a tube fluidly coupled to inlet of the channel as seen in FIG. 2E. For example, a motorized syringe pump can be used for driving the analyte flows into and out of the microfluidic channel through an inlet tube coupled to the inlet 31 and an outlet tube coupled to the outlet 33 (e.g., tube diameter: 0.75 mm). Such a setup can enable stable laminar flows of analyte solutions and minimize the noise induced by the liquid loading processes, which is required for precisely analyzing the real-time kinetic processes of antibody-(TNF-α) binding. Other arrangements for constructing a fluidic channel are also contemplated by this disclosure.

Next, sensor responses were measured from different TNF-α concentrations under the thermodynamic equilibrium condition. At the beginning of the measurement, deionized (DI) water is injected into the biosensor 10 with flow rate of 5 μL/min. At the same time, the FET 14 is biased under a given set of $V_G$ and $V_{DS}$ by a controller (e.g., a microcontroller) interfaced with the FET 14. After the $I_{DS}$ value is stabilized, the analyte solution with a specific TNF-α concentration is injected into the sensor. For each biosensor, the static transfer characteristics (i.e., drain-source current ($I_{DS}$)–back gate voltage ($V_G$) curves acquired under a fixed drain-source voltage ($V_{DS}$)) were measured at each of the biodetection stages by the controller. Measurements followed the sequence of (1) bare transistor, (2) antibody functionalization, and inputs of TNF-α solutions with concentrations of (3) 60 fM, (4) 300 fM, (5) 600 fM, (6) 3 pM, and (7) 6 pM. To eliminate the effect of the $I_{DS}$-$V_G$ hysteresis, all $I_{DS}$-$V_G$ curves were measured by sweeping $V_G$ from −100V to 100V with a sweep rate of 10V/s. Other details about different biodetection stages and transistor characterizations are described later in this disclosure.

Figure 3A:
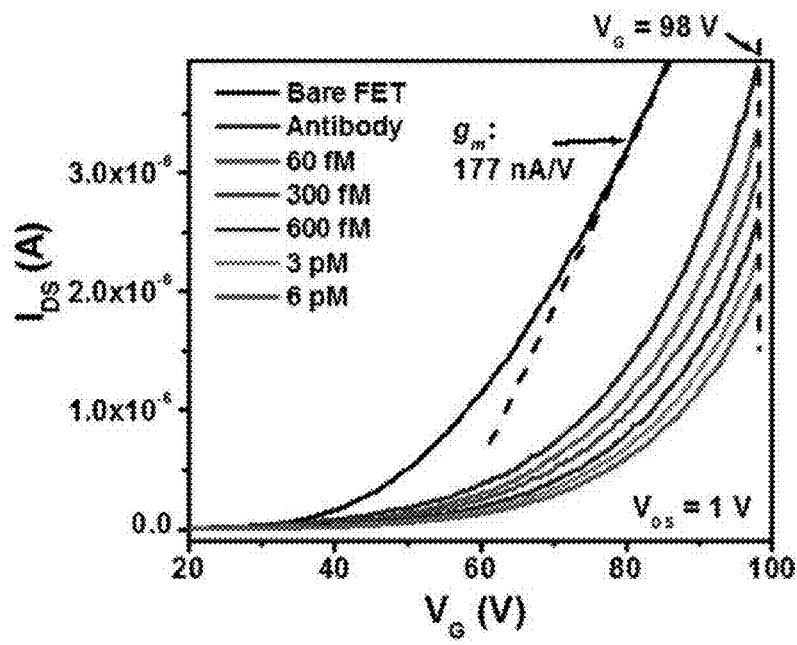
FIG. 3A is a graph depicting transfer characteristics of the exemplary biosensor measured in the linear transport regime at various biodetection stages.

FIG. 3 displays the sensor responses measured in the linear transport regimes of biosensors. Specifically, FIG. 3A shows the transfer characteristics of the exemplary sensor 10 measured at various biodetection stages. Here, $I_{DS}$ data are plotted in the linear scale. The transfer characteristics of this sensor exhibit a strong dependence on TNF-α concentrations, and the TNF-α detection limit is estimated to be ~60 fM. A fixed $V_G$ is chosen within the linear regimes of all $I_{DS}$-$V_G$ curves (e.g., $V_G$=98 V, as denoted by the dashed vertical line in FIG. 3A). The $I_{DS}$ values measured under the $V_G$ vary according to different biodetection states and such $I_{DS}$ data could be utilized as a sensor response signal. However, such a response signal is highly dependent on the transistor performance parameters (e.g., transconductance) ($g_m$) and a threshold voltage ($V_T$). Therefore, in the analysis of a given biodetection state, the $I_{DS}$ signals acquired by different MoS$_2$ transistors may exhibit a poor device-to-device consistency due to the nonuniformity of MoS$_2$ transistors. Although such an issue could be mitigated through optimizing the material deposition and device fabrication processes, a calibrated sensor response quantity independent of the device performance is highly desirable.

The linear regime of an $I_{DS}$-$V_G$ characteristic curve measured from a microscale MoS$_2$ transistor sensor in a specific biodetection state can be expressed as Equation (1). In these experiments, it is observed that for a given transistor sensor, the $g_m$ values extracted from different $I_{DS}$-$V_G$ curves that correspond to different biodetection states are very close and can be approximated as a constant for this sensor. For example, the $g_m$ value of the sensor shown in FIG. 3A is extracted to be ~177 nS at $V_{DS}$=1 V. Based on this observation and Equation (1) as well as the implication from previous works done by Duan et al. and Ishikaw et al, a calibrated sensor quantity (S) is derived and expressed in Equation (2), where $I_{DS(anti)}$ is the $I_{DS}$ value measured in the "antibody functionalization" state of a sensor biased under a set of fixed $V_{DS}$ and $V_G$, and $I_{DS}$-$I_{DS(anti)}$ indicates the $I_{DS}$ variation induced by the introduction of TNF-α molecules. Such an $I_{DS}$ variation normalized by the $g_m$ of this sensor results in a sensor response quantity directly related to the change in the $V_T$ of the sensor (i.e., $\Delta V_T$). It should be noted that although $\Delta V_T$ is assumed to be completely induced by the charge brought to the HfO$_2$ effective layer on top of the transistor channel through antibody-(TNF-α) binding events, $\Delta V_T$ is not exactly the binding-event-induced potential change ($\Delta \phi$) on the effective layer. This is because in this work, $\Delta V_T$ is the change in the $V_T$ measured from the back gate. However, $\Delta V_T$ and $\Delta \phi$ can be related by $\Delta V_T = (C_{HfO2}/C_{SiO2})\Delta\phi$, where $C_{SiO2}$ and $C_{HfO2}$ are the capacities of the SiO$_2$ back gate dielectric and the HfO$_2$ effective layer, respectively. Based on this model, $\Delta V_T$ can be evaluated using $\Delta V_T = qd_{SiO2}\sigma TNF/k_{SiO2}\epsilon_0$, where q is the effective charge carried by a TNF-α molecule (the screening effect due to the buffer liquid has been incorporated into q); $d_{SiO2}$ and $k_{SiO2}$ are the thickness and dielectric constant of the SiO$_2$ back-gate dielectric layer, respectively, $\epsilon_0$ is the vacuum permittivity; and $\sigma_{TNF}$ is the areal density of TNF-α molecules bound to the antibody receptors functionalized on the effective layer. Therefore, such a calibrated response quantity (S) is proportional to the antibody receptor occupancy at the equilibrium state and it is also independent of the MoS$_2$ transistor performance. These two conditions are critical for the subsequent Langmuir isotherm analysis.

$$I_{DS} = g_m \left( V_G - V_T \frac{V_{DS}}{2} \right) \quad (1)$$

$$S = -\frac{I_{DS} - I_{DS(anti)}}{g_m} = \Delta V_T = \frac{qd_{SiO2}\sigma_{TNF}}{K_{SiO2}\epsilon_0} \quad (2)$$

Figure 3B:
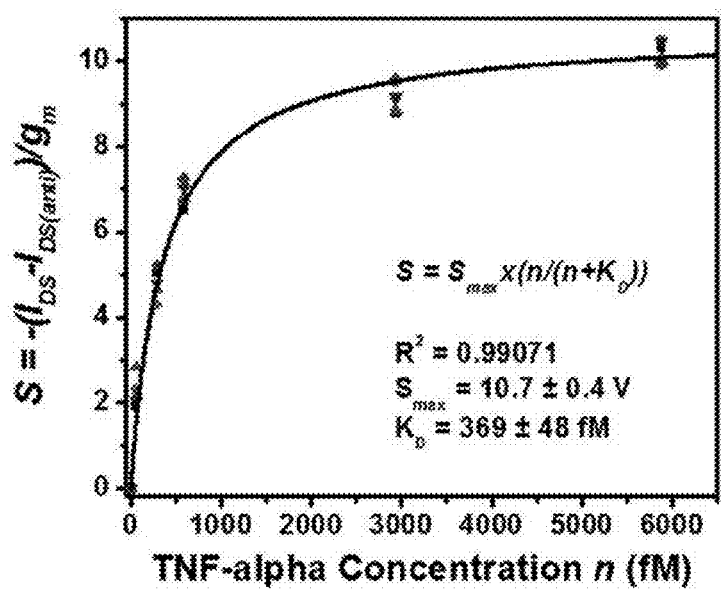
FIG. 3B is a graph depicting a set of calibrated linear-regime responses (S) measured from five different biosensors with respect to TNF-α concentration (n)

FIG. 3B plots the calibrated responses measured from the linear transport regimes of the five different sensors with respect to TNF-α concentration (n). Although the transfer characteristics of these five sensors exhibit significant difference in $V_T$, $I_{DS}$ and $g_m$, FIG. 3B shows that the calibrated responses from these sensors are consistent with each other and can serve as a standard curve (i.e., a generic S-n-curve) for TNF-α detection. This standard curve can be well fitted with Langmuir isotherms (Equation (3)) and the affinity equilibrium (or dissociation) constant ($K_D$) of the antibody-(TNF-α) pair is extracted to be 369±48 fM; the maximum sensor response ($S_{max}$) is extracted to be 10.7±0.4V.

$$S = S_{max} \frac{n}{n + K_D} \quad (3)$$

Figure 4A:
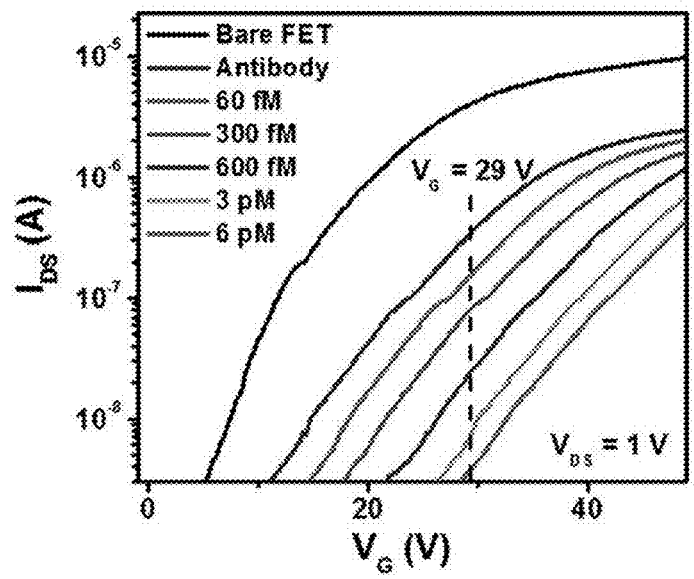
FIG. 4A is a graph depicting transfer characteristics of the exemplary biosensor measured in the subthreshold regimes at various biodetection stages.

Alternatively, sensor responses can also be measured from the subthreshold regimes of MoS$_2$ transistor sensors. In the subthreshold regime of a transistor sensor, the sensitivity of $I_{DS}$ to the variation of electrical potential (or charge) at the effective layer is much higher than that in the linear transport regime of this sensor. Therefore, the responses from the subthreshold regimes of transistor sensors are expected to result in the higher biodetection sensitivity in comparison with those from the linear regimes. FIG. 4A shows the transfer characteristics of another exemplary MoS$_2$ transistor sensor, which were measured at various biodetection stages. Here $I_{DS}$ data are plotted in the logarithmic scale, and the subthreshold regimes are emphasized. A fixed $V_G$ was chosen within the subthreshold regimes of all $I_{DS}$-$V_G$ curves (e.g., $V_G$=29V denoted by the vertical dashed line in FIG. 4A). The $I_{DS}$ values measured under this $V_G$ clearly vary according to different biodetection states and exhibit a strong dependence on TNF-α concentration. Here, the TNF-α detection limit is estimated to be at least as low as 60-fM. Similarly, such $I_{DS}$ data acquired in the subthreshold regimes of transistor sensors cannot be directly used as standard sensor responses. A calibrated subthreshold-regime response quantity independent of the transistor performance is needed.

In the subthreshold regime of a microscale MoS$_2$ transistor sensor, the $I_{DS}$-$V_G$ relationship measured from a specific biodetection state can be approximately expressed by Equation (4), where $I_T$ is the $I_{DS}$ value measured at $V_G$=$V_R$ under a given $V_{DS}$; SS is the subthreshold swing. As observed in these experiments, although the functionalization of a transistor sensor with antibody receptors (i.e., the transition from "bare transistor" to "antibody functionalization" states) can result in an observable reduction of the SS of this sensor, the SS value does not significantly vary among the subsequent biodetection states, including the inputs of TNF-α samples with incremental concentrations. Therefore, for a given as-functionalized transistor sensor, SS can be approximated as a constant. Based on this observation, a calibrated subthreshold-regime sensor response quantity (S) is derived from Equation (4) and expressed in Equation (5), in which $I_{DS(anti)}$ is the drain-source current measured in the "antibody functionalization" state of a sensor biased under a set of fixed $V_{DS}$ and $V_G$; and $I_{DS}$ is the drain-source current measured from a subsequent biodetection state (i.e., a specific TNF-α concentration). Similar to the calibrated linear-regime response quantity expressed in Equation (2), this subthreshold counterpart is also directly related to $\Delta V_T$, independent of the transistor performance, and proportional to $\sigma_{TNF}$.

$$I_{DS} = I_T \times 10^{(V_G - V_T)/SS} \quad (4)$$

$$S = -SS \times \log\left(\frac{I_{DS}}{I_{DS(anti)}}\right) = \Delta V_T = \frac{SiO2^{\sigma} TNF}{k_{SiO2}\varepsilon_0} \quad (5)$$

Figure 4B:
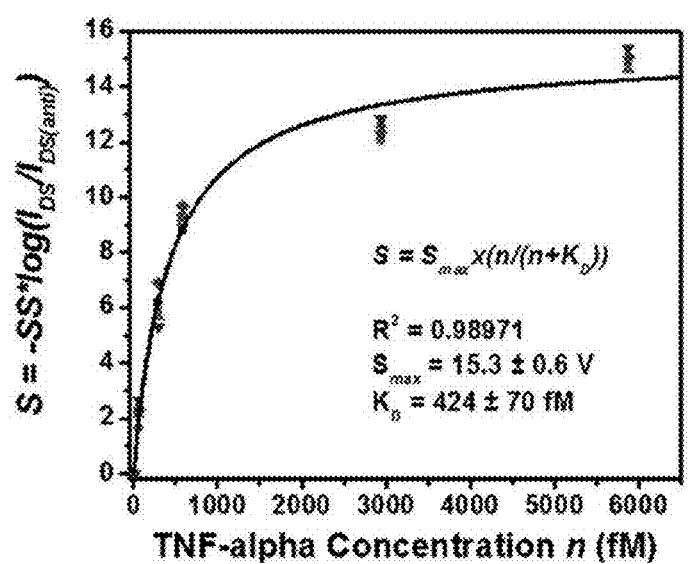
FIG. 4B is a graph depicting a set of calibrated subthreshold-regime responses (S) measured from five different biosensors with respect to TNF-α concentration (n)

FIG. 4B displays the calibrated subthreshold-regime responses (S) measured from five different sensors with respect to TNF-α concentration (n). As shown, the calibrated S-n curves measured from these devices are consistent with each other and can be well fitted with Langmuir isotherms (Equation (3)). Here, the equilibrium constant ($K_D$) of the antibody-(TNF-α) pair is extracted to be 424±70 fM, which is consistent with the $K_D$ value extracted from the linear-regime sensor responses (i.e. 369±48 fM). The $S_{max}$ parameter is fitted to be 15.3±0.6 V, which is about 40% larger than that extracted from the linear-regime responses (i.e., 10.7±0.4 V). This observable discrepancy has not been fully understood. However, this could be temporarily attributed to the different back-gate $V_G$ levels required for biasing sensors in subthreshold and linear regimes, which could result in different magnitudes of electric field penetrating through few-layer MoS$_2$ channels as well as HfO$_2$ effective layers and leaking into the analyte solution. This could lead to different degrees of the modification of electrical-double layers around sensors and therefore different degrees of the screening of the charges brought through analyte-receptor binding pairs.

Although the $I_{DS}$ signals measured from both linear and subthreshold regimes can be mathematically normalized to consistent device-independent response quantities using Equations (2) and (5), the physical limit-of-detection of a transistor biosensor is indeed determined by the sensitivity of $I_{DS}$ to the variation of analyte concentration (dn) as well as the noise level of electrically measured $I_{DS}$ signals. This $I_{DS}$ sensitivity is quantitatively defined as the relative change in $I_{DS}$ per change in n (i.e., $$\left(i.e., \text{Sensitivity} = \frac{dI_{DS}}{I_{DS}} \bigg/ dn\right).$$

Figure 5A:
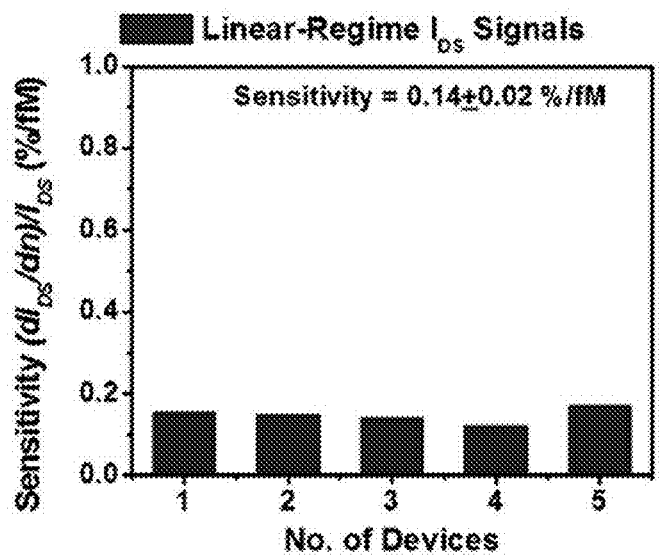
FIGS. 5A and 5B are graphs depicting sensitivity data acquired from the linear-regime $I_{DS}$ signals measured from the five sensors and the subthreshold-regime $I_{DS}$ signals measured from the five sensors, respectively.
Figure 5B:
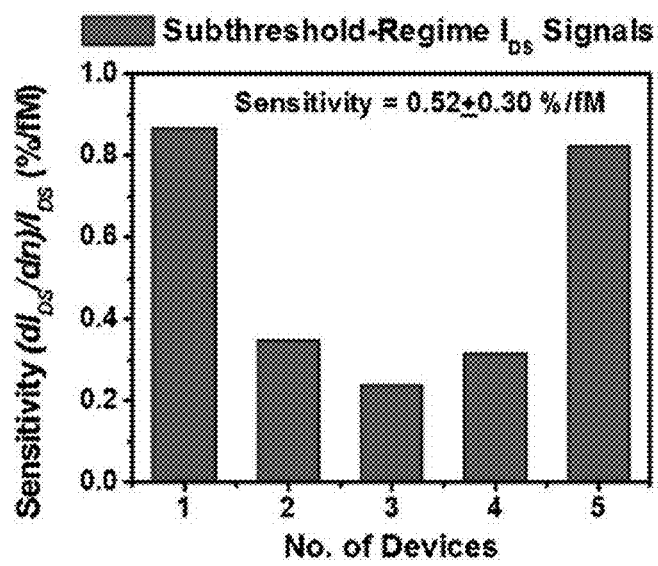

FIG. 5 displays and compares the sensitivity data acquired from (a) the linear-regime $I_{DS}$ signals measured from the five sensors and (b) the subthreshold-regime $I_{DS}$ signals from the five sensors. All differential sensitivity values are evaluated at TNF-α concentration of n=60 fM. This can provide critical information about the sensitivity required for obtaining fM-level detection limits. FIG. 5 shows that the subthreshold-regime $I_{DS}$ sensitivities (0.52±0.3%/f.M) are statistically higher than the linear-regime $I_{DS}$ sensitivities (0.14±0.02%/fM). Therefore, subthreshold-regime sensor responses are more desirable in achieving high detection sensitivity. However, it should be noted that the ultimate detection limit of a transistor sensor is also limited by the signal-to-noise ratios of electrically measured $I_{DS}$ signals. In addition, for detecting low-abundance molecules, the non-specific adsorption of target molecules could also strongly affect the detection limit. Finally, it is also noted that the sensitivity data listed in FIG. 5B exhibit the larger device-to-device variation in comparison with those listed in FIG. 5A. This is probably because of the threshold swing properties of MoS$_2$ transistors are more sensitive to the fabrication introduced defects than their linear-regime transconductance properties. Therefore, for the current MoS$_2$ transistors, their linear-regime $I_{DS}$ signals (or linear-regime transconductances) exhibit the higher device-to-device consistency than their subthreshold-regime $I_{DS}$ signals.

Figure 6A:
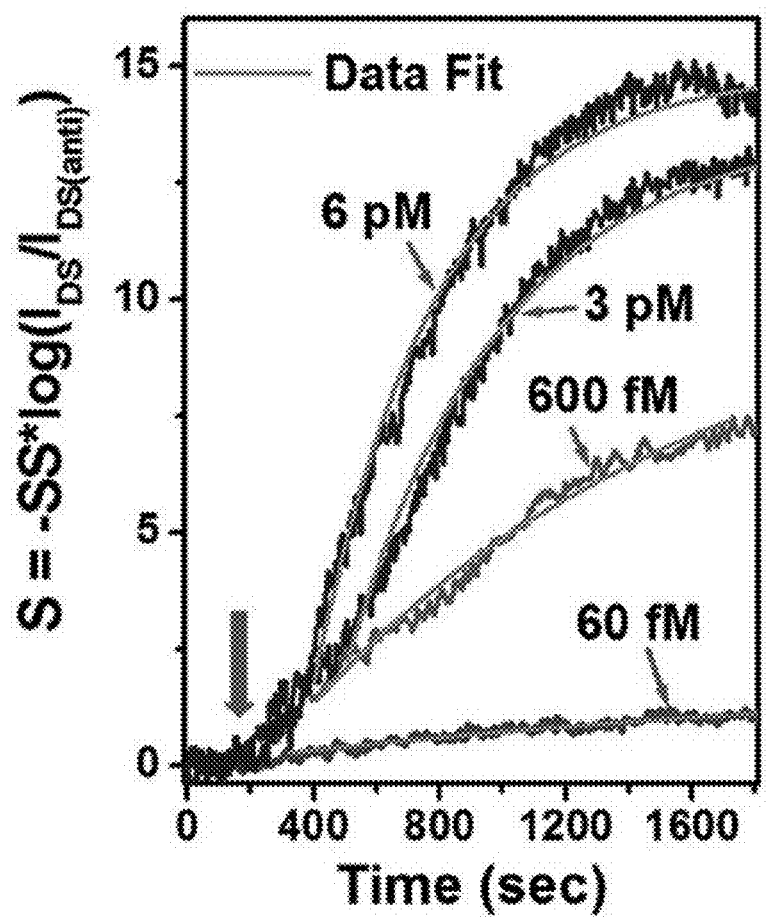
FIG. 6A is a graph depicting real-time sensor responses of antibody-(TNF-α) binding measured under different TNF-α concentration.

To evaluate the detection specificity of our $MoS_2$ transistor sensors, a sensor functionalized with anti-human TNF-α antibody is used for detecting interleukin-6 (IL-6) cytokine. The biosensor setup shown in FIG. 2C is used for measuring the time-dependent association/dissociation kinetics of the antibody-(TNF-α) pair. FIG. 6A displays real-time sensor responses of antibody-(TNF-α) binding measured under different TNF-α concentrations (i.e., n=60 fM, 600 fM, 3 pM, and 6 pM). Each of the time-dependent response curves was measured from a different $MoS_2$ transistor sensor and all as-measured $I_{DS}$ responses were normalized using S=SS× $(I_{DS}/I_{DS(anti)})$ (i.e., Equation (5) for calibrating subthreshold-regime responses). In FIG. 6A, the red arrow indicates the onset time, at which the solutions with specific TNF-α concentrations were filled into the respective biosensors. The real-time response curves in FIG. 6A show that the association rate of the antibody-(TNF-α) pair increases with increasing TNF-α concentration. The rise segment of each real-time response curve can be well fitted with the first-order absorption equation (i.e., Equation (6)). In Equation (6), $S_{eq}$ is the sensor response at the final equilibrium state; $k_{on}$ and $k_{off}$ are association and dissociation rates, respectively; $k_{on}n+k_{off}$ relates to the rising slope of the linear regime of the response curve. Table-1 lists the fitting results of $S_{eq}$ and ($k_{on}n+k_{off}$) parameters for n=60 fM, 3 pM, and 6 pM.

TABLE 1

| | n-60 fM | 600 fM | 3 pM | 6 pM |
|---|---|---|---|---|
| $S_{eq}(V)$ | 2.07 ± 0.03 | 10.7 ± 0.5 | 13.9 ± 0.06 | 14.7 ± 0.13 |
| $(k_{on} \pm k_{off})(s^{-1})$ | (3.68 ± 0.15) × $10^{-4}$ | (6.94 ± 0.46) × $10^{-4}$ | (1.74 ± 0.10) × $10^{-3}$ | (3.28 ± 0.10) × $10^{-3}$ |

Figure 6B:
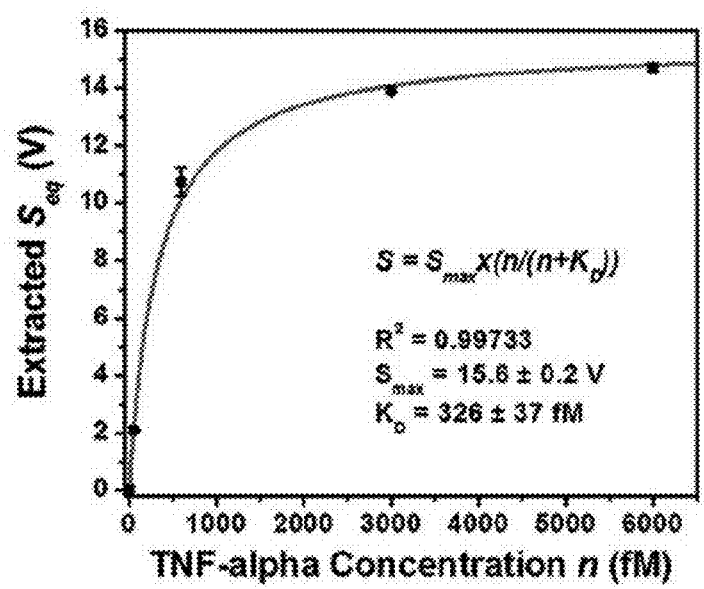
FIG. 6B is a graph depicting the equilibrium-state responses ($S_{eq}$) extracted from this fit plotted as a function of TNF-α concentration, which can be further fitted with Langmuir isotherm.

These $S_{eq}$ values extracted from the real-time binding responses are consistent with the sensor responses directly measured at the equilibrium state, that is, after a long incubation of ~2 hours (e.g., the equilibrium-state response date shown in FIG. 4B). In particular, FIG. 6B plots the extracted $S_{eq}$ data as a function of TNF-α concentration which can be also fitted with Langmuir isotherm. Here, the equilibrium constant ($K_p$) is extracted to be 326±37 fM and the maximum response ($S_{max}$) is extracted to be 15.6±0.2V, which are consistent with those extracted from the equilibrium-state subthreshold-regime responses shown in FIG. 4B.

$$S = S_{eq}(1 - e^{-(k_{on}n+k_{off})t}) \quad (6)$$

Figure 6C:
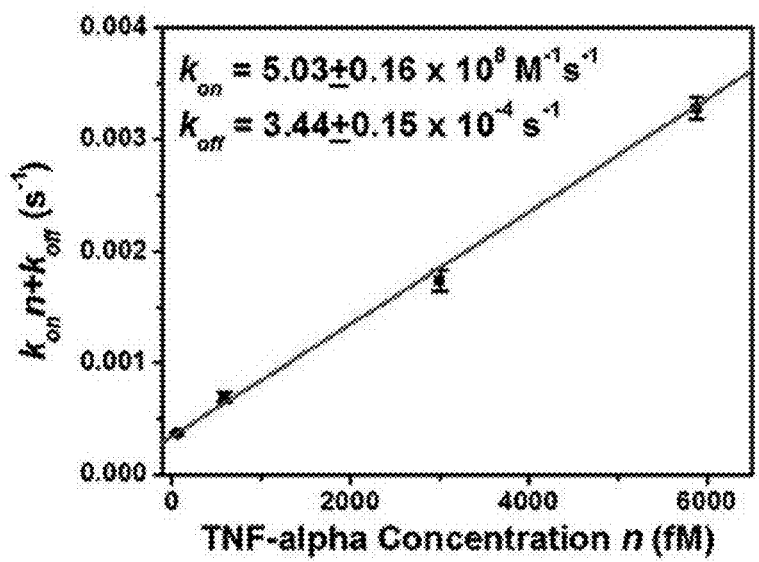
FIG. 6C is a graph depicting the extracted ($k_{on} n + k_{off}$) data plotted as a function of TNF-α concentration (n)
Figure 7:
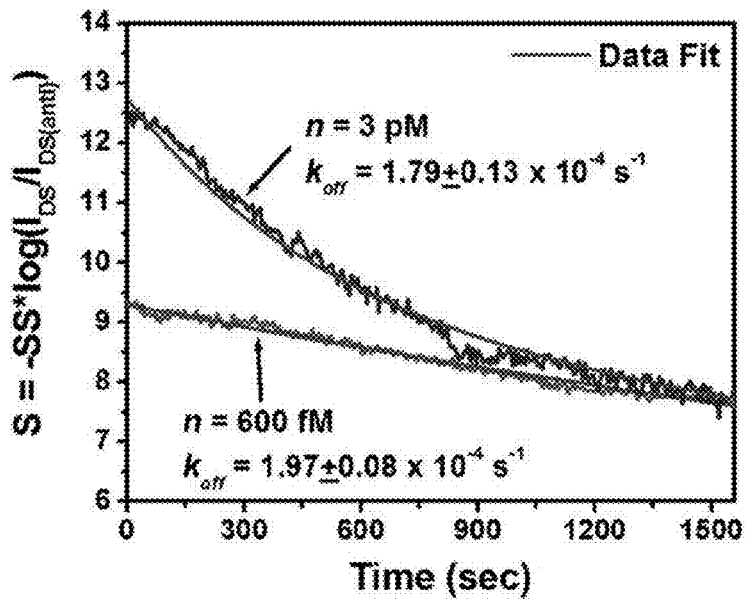
FIG. 7 is a graph illustrating time-dependent dissociation kinetics of the antibody-(TNF-α) pair measured from two biosensors that were incubated in solutions with TNF-α concentration.

To evaluate $k_{on}$ and $k_{off}$ parameters, the extracted ($k_{on}n+k_{off}$) data are plotted as a function of TNF-α concentration (n) (see FIG. 6C). The linear fitting results in rate constants of $k_{on}=(5.03\pm0.16)\times10^8 M^{-1} s^{-1}$ and $k_{off}=(3.44\pm0.15)\times10^{-4} s^{-1}$. It should be noted that this fit is not sensitive to the dissociation rate ($k_{off}$) because of its small numerical value. To achieve a more precise quantification rate of $k_{off}$, the real-time dissociation kinetics of the antibody-(TNF-α) pair was directly measured. Specifically, two as-functional $MoS_2$ transistor biosensors were incubated in solutions with TNF-α concentration of 600 fM and 3 pM, respectively. The incubation time was more than 2 hours as that antibody-(TNF-α) association/dissociation processes reached to the equilibrium state. Afterwards, these fully incubated sensors were rinsed with pure buffer liquid flow and the calibrated sensor responses were recorded as a function of the lapsed time, as displayed in FIG. 7. FIG. 7 shows that the sensor responses decreased with time, which was attributed to unbinding events. The response curve measured from the device incubated with TNF-α concentration of 600 fM can be well fitted with a monoexponential decay function (i.e., the desorption equation expressed in Equation 7)). In Equation (7), S, represents the sensor response corresponding to the areal density of bound molecule residues after the desorption process. This fit results in $k_{off}=(1.97\pm0.08)\times10^{-4}$ $s^{-1}$, from which the affinity equilibrium constant $K_D$ can be also estimated to be $K_D=k_{off}/k_{on}=392$.fM. This $K_D$ value is also consistent with those extracted from the equilibrium-state sensor responses (i.e., $K_D$ values extracted from FIGS. 3 and 4). From this fit, S, is extracted to be 3.0±0.2 V and $S_{eq}$ is 9.2±0.4 V. This implies that ~30% of bound TNF-α molecules are expected to remain absorbed on the sensor even after a long rinsing process.

$$S = (S_{eq} - S_r)e^{-k_{off}t} + S_r \quad (7)$$

$$S = (S_{eq} - S_2 - S_r)e^{-k_{off}t} + S_2 e^{-k_2 t} + S_r \quad (8)$$

The response curve measured from the device incubated with the TNF concentration of 3 pM can be hardly fitted with monoexponential Equation (7). Note that it can be fitted with a bi-exponential decay equation (Equation (8)). This fit results in $S_{eq}=13.6\pm1.0$ V, $S_2=4.5\pm0.2$ V, $S_r$, =2.9±0.3 V, $k_2=(2.0+0.16)\times10^{-3}$ $s^{-1}$, and $k_{off}=(1.79\pm0.13)\times10^{-4}$ $s^{-1}$. As reported by several previous works, such a bi-exponential behavior of sensor responses is probably due to the multi-valent antigen-antibody binding, which may become more prominent with increasing the analyte concentration. This explanation is reasonable because the antibody used in this work is polyclonal. To fully understand the association/dissociation kinetics of multivalent binding/unbinding processes, a more complicated model for describing antibody-(TNF-α) binding is needed.

Figure 8:
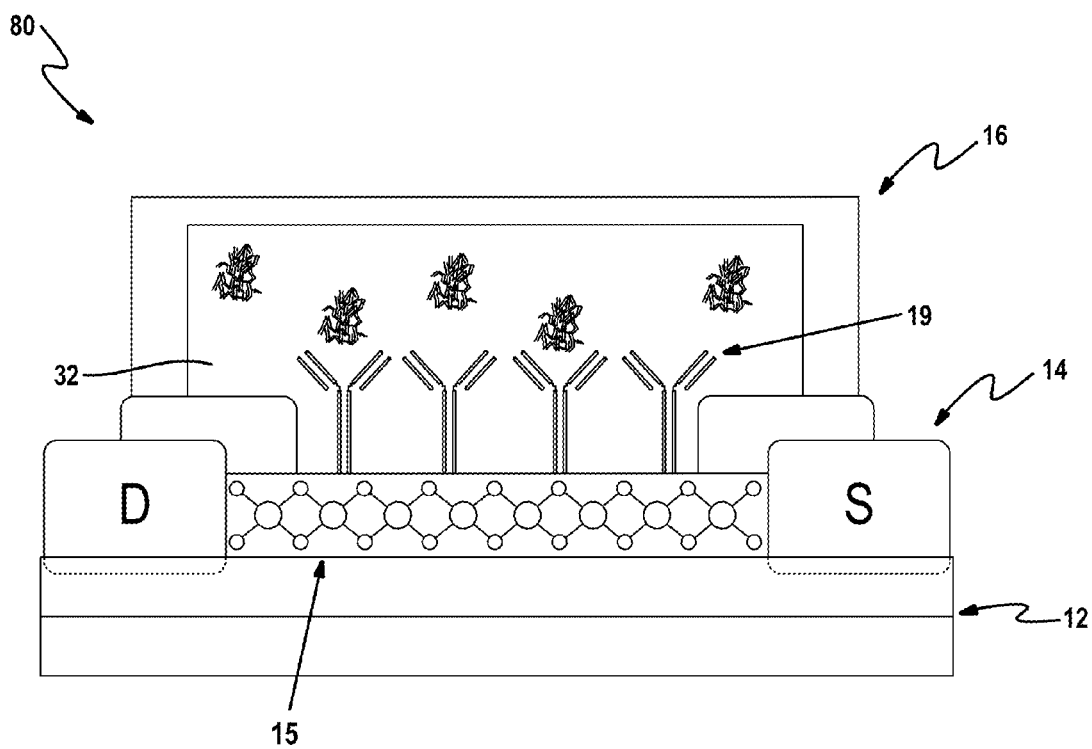
FIG. 8 is a cross-sectional view of another example embodiment of an insulating-layer-free biosensor.

FIG. 8 depicts another example embodiment of a biosensor 80 which employs an atomically thin channel structure. In a similar manner, the biosensor 80 is comprised of a field effect transistor (FET) 14 formed on a substrate 12 and a reservoir layer 16 integrated on top of the FET 14. In this embodiment, the insulating layer is omitted. That is, the antibody 19 is functionalized directly onto the exposed surface of the channel region of the FET 14. Except with respect to the differences discussed herein, the biosensor 80 may be substantially the same as the biosensor 10 described above.

Figure 9A:
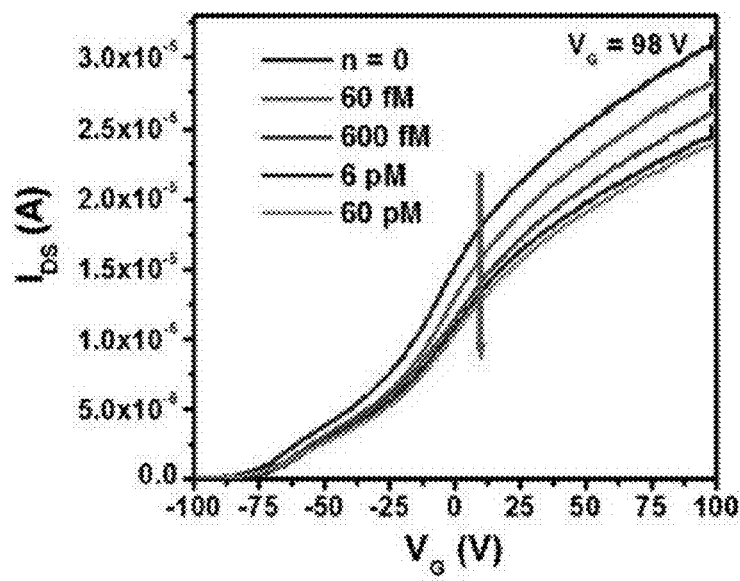
FIG. 9A is a graph depicting transfer characteristics of the insulating-layer-free sensor.
Figure 9B:
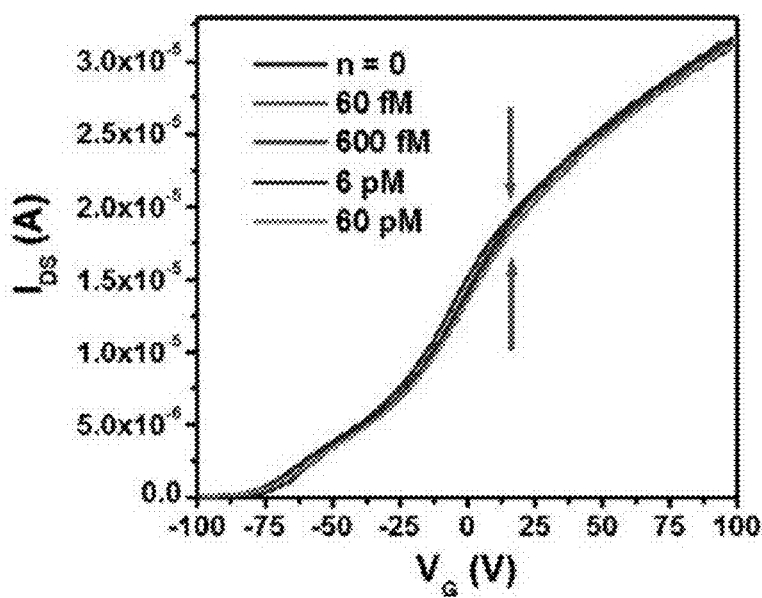
FIG. 9B is a graph depicting transfer characteristic curves from FIG. 9A coincidental with each other.

FIG. 9A displays the transfer characteristics of the exemplary insulating-layer-free biosensor 80, measured by the controller from n=0, 60 fM, 600 fM, 6 pM, and 60 pM. This sensor exhibited a very different response behavior from insulating-layer-coated sensors 10. With increasing n, the $I_{DS}-V_G$ curve of this sensor did not significantly shift along the $V_G$ axis, but exhibited a proportional scale-down along the $I_{DS}$ axis (i.e., the $I_{DS}$ (or $g_m$) values proportionally decreased with increasing n). Such a proportional reduction of $I_{DS}$ (or $g_m$) values can be further verified by the fact that we can make all $I_{DS}-V_G$ curves from different TNF-α concentrations coincide by multiplying their $I_{DS}$ values with appropriate factors, as shown in FIG. 9B. This result indicates that when TNF-α molecules are bound to an insulating-layer-free sensor, they can result in reduction of the $g_m$ (or the mobility) of the FET. Such a response behavior cannot be described by the simple capacitor model. For such insulating-layer-free sensors, a tentative calibrated response quantity is the relative change of the ON-state $I_{DS}$ under a given $V_G$, as expressed by the following equations:

$$S = \frac{I_{DS} - I_{DS(n=0)}}{I_{DS(n=0)}} \quad (9)$$

As demonstrated, both insulating-layer-coated and insulating-layer-free sensors can result in a limit-of-detection (LOD) not higher than 60 fM for TNF-α detection. However, the employment on insulating-layer-free sensors can simplify the fabrication of MoS$_2$ FET immunoassay chips. In addition, bare MoS$_2$ sensing areas are naturally hydrophobic and could enable the direct functionalization of a broad variety of antibodies without using complicated linkers, therefore simplifying the functionalization process.

In spite of the simplicity of insulating-layer-free sensors, to ultimately realize biomarker quantification using such sensors, one needs to understand the device physics governing their response behavior. The antigen/antibody-binding-induced reduction of the $g_m$ values of the insulating-layer-free sensors 80 (FIG. 2(c)) is attributed to the biomolecule-induced disordered potential in the MoS$_2$ channels, which can reduce the FET mobility. To support this hypothesis, quasi-quantitatively simulated the electrostatic potential distribution in the MoS$_2$ channels, which is induced by the charged antigen-antibody pairs. The simulation was performed using an electromagnetics simulation software (Maxwell™) based on finite-element analysis. In this simulation, the antigen-antibody pairs were modeled as charged pillars randomly and discretely distributed on the sensors (pillar diameter: 4 nm, height: 10 nm, and minimum spacing between pillars: 10 nm). Such a simple model of antigen-antibody pairs is approximately consistent with the geometric dimensions and spatial spacing of real antibody-(TNF-α) pairs bound to a solid sensor surface.

Figure 10A:
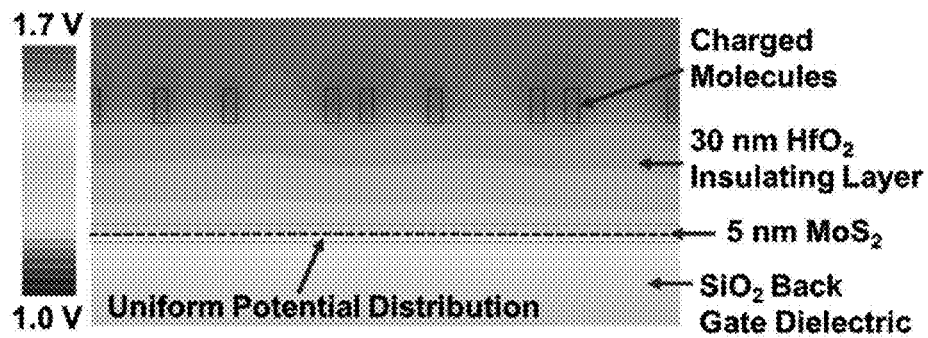
FIGS. 10A and 10B illustrate simulation of the electrostatic potential distribution in the channel region of the insulating-layer-coated sensor and the insulating-layer-free sensor, respectively.
Figure 10B:
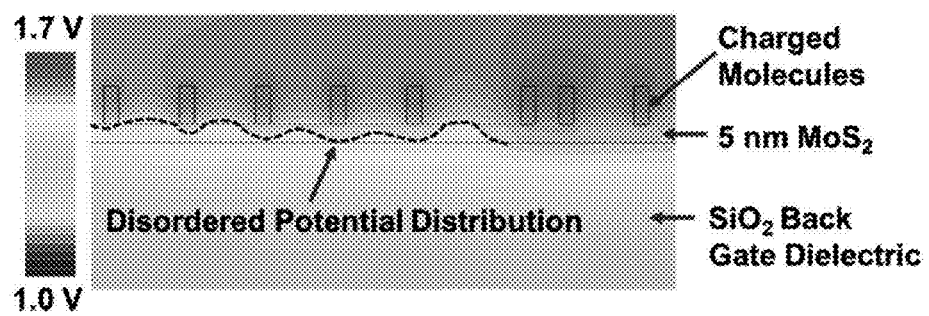

FIGS. 10A and 10B shows the simulated potential distributions in the MoS$_2$ channels of (a) an insulating-layer coated sensor 10 and (b) an insulating-layer-free sensor 80, respectively. For both sensors, the charged molecules induce disordered and corrugated equipotential surfaces in the proximity of molecules. For the insulating-layer-coated sensor, the presence of a 30 nm HfO$_2$ insulating layer can effectively buffer such a disordered potential distribution and result in relatively flat equipotential surfaces in the MoS$_2$ channel. Such a uniform field distribution in the MoS$_2$ channel does not significantly modulate the carrier mobility (or $g_m$) but only induces a $\Delta V_T$. For the insulating-layer-free sensor, the molecules directly generate a disordered/corrugated potential distribution in the MoS$_2$ channel, which is expected to significantly enhance the scattering and localization probabilities of moving carriers, therefore degrading the carrier mobility (and $g_m$) of the FET. In 2D monolayer or quasi-2D few-layer MoS$_2$ FET channels, such a disordered potential effect is expected to be more prominent than that in bulk semiconductors because of the 2D confinement of carriers. This simulation result can qualitatively explain the response behavior of the insulating-layer-free sensors.

Figure 11:
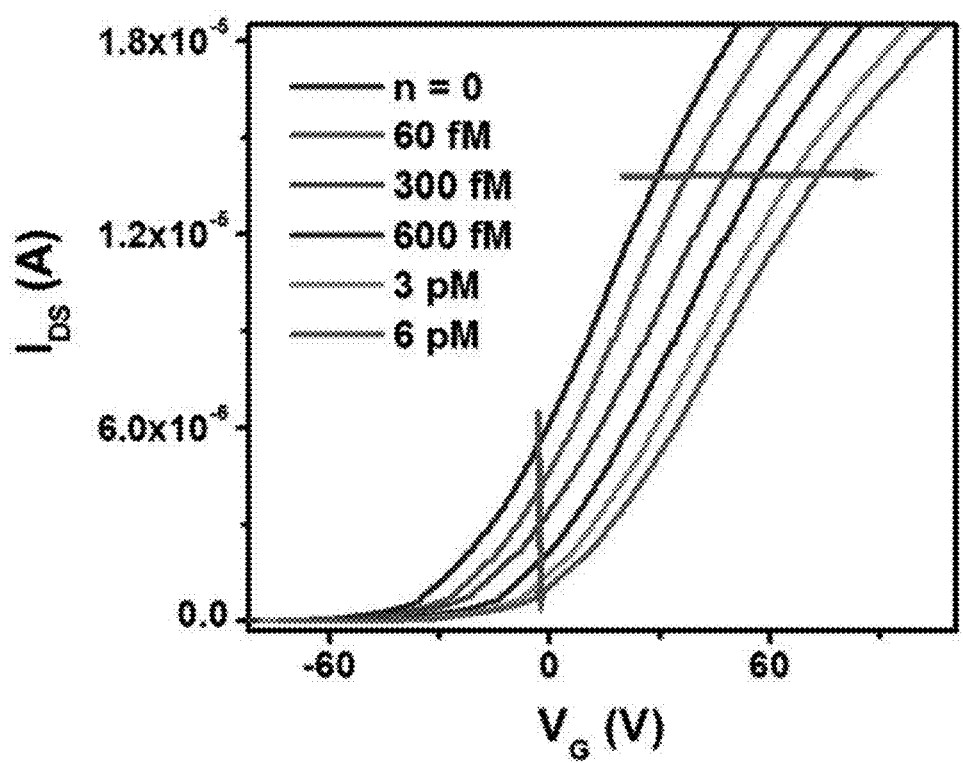
FIG. 11 is a graph depicting transfer characteristics of the biosensor with a 5 nm thick insulating layer measured at various TNF-α concentrations.

Additionally, simulation implies a critical al HfO$_2$ layer thickness of $t_c$~5 nm. When the HfO$_2$ layer thickness t is thinner than $t_c$, the biomolecule-induced potential disorder is prominent in the MoS$_2$ channel and the FET is expected to function as a $g_m$-modulated sensor, as demonstrated in FIGS. 9A and 9B. When $t_{HfO2}$ is thicker than $t_c$, the potential distribution in the MoS$_2$ channel is uniform and the FET is expected to function as a $V_T$-modulated sensor. It is further speculated that when $t_{HfO2}$ is close to $t_c$, the sensor may exhibit a hybrid response behavior involving both $g_m$ and $V_T$ modulations. To test this speculation, additional sensors were fabricated with $t_{HfO2}$=5 nm~$t_c$. FIG. 11 shows the transfer characteristics of one of such sensors. With increasing TNF-α concentration, the $I_{DS}$-$V_G$ curve of this sensor indeed underwent a shift toward the positive $V_G$ direction in concurrent with a drop of the $g_m$. This indicates that the sensors with $t_{HfO2}$~$t_c$ exhibit a hybrid $g_m$/$V_T$-modulated character. Such a response behavior can be further confirmed by the fact that we can make all $I_{DS}$-$V_G$ curves coincide by shifting them along the $V_G$-axis and subsequently multiplying them with different factors. This result strongly supports the simulation model and further implies that HfO$_2$ layer thickness strongly affects the potential disorder in the MoS$_2$ channels and determines the sensor response characters.

Figures 12A, 12B, 12C, 12D, 12E:
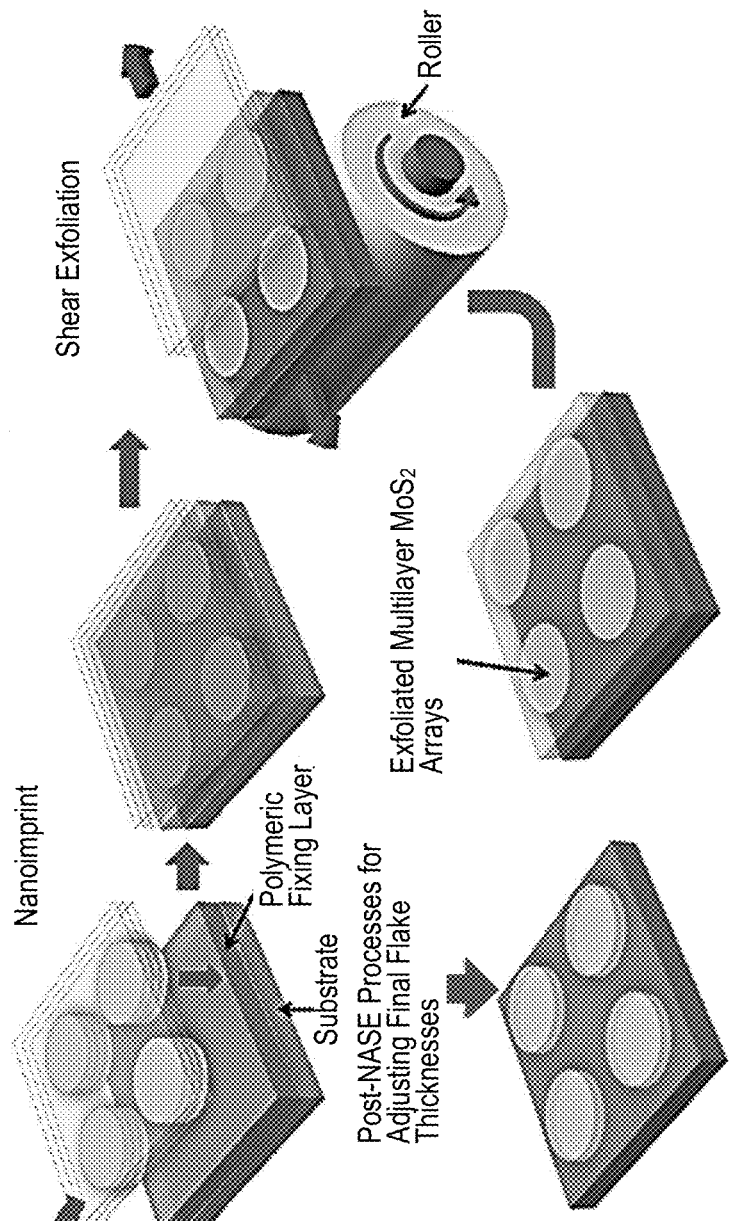
FIGS. 12A-12E are diagrams illustrating a proposed nanoimprint-assisted shear exfoliation (NASE) process.

In another aspect of this disclosure, a method is presented for producing multilayer channel regions (i.e., MoS$_2$ flake arrays) with uniform thicknesses. With reference to FIGS. 12A-12D, a nanoimprint-assisted shear exfoliation (NASE) technique is described. First, a bulk MoS2 ingot is pre-structured with protrusive multilayer mesa arrays by using photolithography followed with plasma etching as seen in FIG. 12A. After this process, this ingot becomes a bulk MoS2 stamp. Further details regarding the MoS2 stamp fabrication have been reported by Nam, H. et. al. in "MoS2 Transistors Fabricated via Plasma-Assisted Nanoprinting of Few_layer MoS2 Flakes into Large-Area Arrays" ACS Nano 2013, 7, 5870-5881. Here, the height of protrusive mesas can be well controlled by adjusting the plasma etching duration. This mesa height will determine the imprint depth (dNIL) resulted by the stamp. When the stamp is ready, a substrate (e.g., glass, Si, or SiO2) is spin-coated with a polymeric fixing layer (e.g., thermoplastics or cross-linkable polymers), and the MoS2 stamp is subsequently pressed into the fixing layer on the substrate through a nanoimprint lithography (NIL) process as seen in FIG. 12B.

Afterwards, a lab-made motorized roller tool is used to displace the MoS2 stamp along the substrate surface (i.e., a shear direction). Due to the shear displacement, the multilayer MoS2 mesas already imprinted into the fixing layer can be exfoliated away from the bulk stamp as seen in FIG. 12C. The roller tool is comprised of an AC brushless motor with an electric speed controller, a flat sample holder for immobilizing either the stamp or the substrate, a motor-driven roller for generating the relative shear displacement between the stamp and the substrate, and a vertical stage for applying a gauge pressure to maintain the stamp flat during the shear exfoliation. The main roller (diameter: 60 mm; width: 150 mm) is responsible for generating the relative shear displacement between a stamp/substrate pair. It was made of aluminum alloy and coated with a 3 mm thick urethane rubber layer to provide a conformal contact between the roller and the flat sample holder as well as enhance the friction between the roller and the stamp (or the substrate). The vertical stage can generate adjustable gauge pressure (or force) between the roller and the flat sample holder (or between the MoS2 stamp and the imprinted substrate). In a typical NASE process, this vertical force is adjusted to be ~200 N. The roller is driven by a brushless motor, which is coupled with an electric speed controller to provide continuous variation of rotation speed. The web speed measured at the roller surface can be controlled within a range of 0 to 30 mm/sec. In a typical NASE process, this speed is adjusted to be ~1 mm/sec, and the typical operation time for a shear exfoliation cycle is 1-5 sec. The thicknesses of exfoliated multilayer flakes are anticipated to be mainly determined by the imprint depth (dNIL) (FIG. 12D). In comparison with previously reported exfoliation methods for generating layered materials, the unique shear exfoliation mechanism involved in NASE can result in significantly improved transfer-printing efficiency of pre-structured MoS2 features as well as higher uniformity of exfoliated MoS2 feature thicknesses. In comparison with chemical synthesis approaches for generating multilayer MoS2, NASE is able to produce MoS2 structures with larger average crystal domain size (10 s-100 s µm), higher ordering of interlayer stacking configurations, and therefore better transport properties. Furthermore, NASE could be further generalized for producing high-quality multilayer structures of other atomically layered materials, such as highly ordered pyrolytic graphite (HOPG) and emerging topological insulators (e.g., Bi2Se3 and Bi2Te3).

After a NASE process, additional etching/ablation processes could be subsequently used for further adjusting the thicknesses of NASE-produced MoS2 flakes to meet the requirements of various device applications as seen in FIG. 12E, such as monolayers for light-emitting devices, 10-50 nm thick flakes for making high-mobility transistors, and 50-200 nm flakes for photovoltaic/photodetection devices. In this disclosure, MoS2 was chosen as the test-bed material for investigating NASE processes, because (i) MoS2 is the most widely studied TMDC material; (ii) MoS2 and other TMDCs share very similar mechanical properties, which makes the nanofabrication processes developed in this work generally applicable to all other TMDCs and layered materials. It is understood that the NASA process is applicale to other types of TMDC materials.

FIG. 13A shows four optical micrographs of NASE-produced MoS2 flakes, which were exfoliated into a 55 nm thick polystyrene (PS) fixing layer coated on a SiO2/Si substrate (SiO2 thickness, 300 nm). These micrographs were captured from different locations over the whole NASE-processed area (~1 cm2), as mapped in the inset photograph of the whole NASE sample. Raman spectroscopy was performed to identify the existence of exfoliated MoS2 flakes in the imprinted PS layer. Our Raman results show that more than 80% of imprinted wells in the PS fixing layer have MoS2 flakes. FIG. 13B shows a typical Raman spectrum of a NASE-produced MoS2 flake, which exhibits two characteristic peaks, A1g and E2g, corresponding to the out-of-plane and in-plane vibration modes of MoS2 layers, respectively. For all NASE-produced MoS2 flakes, their A1g-E2g peak spacings are larger than 19 cm-1. This indicates that all NASE-produced flakes are multilayer MoS2 structures. The OM and Raman characterizations show that NASE can produce orderly arranged multilayer MoS2 device structures over cm2-scale areas. Although most imprinted well pixels in PS fixing layers have high-quality MoS2 flakes faithfully exfoliated from the bulk stamps, observable imperfection features still occur during NASE processes. FIG. 13C displays the OM images of typical imperfection features occurring in NASE, which includes (i) imprinted PS wells without MoS2 (i.e., no exfoliation), (ii) imprinted wells with broken MoS2 fragments (i.e., incomplete exfoliation), (iii) MoS2 dislocated away from the imprinted PS wells, and (iv) non-uniform thickness distribution within individual flakes. The occurring probabilities of these imperfection features may be relevant to mechanical properties of TMDC stamps and polymeric fixing layers, flatness/total size of TMDC stamps, geometric dimensions of pre-structured TMDC structures, and NASE processing parameters (e.g., roller speed and vertical pressure), etc. Especially, it was found that the aspect ratio (i.e., the ratio of the height to the lateral size of a feature) of protrusive mesas pre-structured on TMDC stamps greatly affects the quality of NASE-produced flakes. In particular, given a fixed lateral size of mesas of 15 µm, the current NASE system can easily exfoliate 40-200 nm high MoS2 mesas without resulting in significant imperfections. However, when the initial mesa thickness (or height) is thinner than 40 nm, the occurring probability of broken, wrinkled, and dislocated mesa flakes is significantly increased. Therefore, as mentioned above, the better route for producing 0.7-40 nm thick, 15 µm size MoS2 flake arrays (i.e., monolayer to 60-layer structures) is to employ NASE for producing uniform flake arrays thicker than 40 nm, and subsequently perform a post-NASE etching process to thin the NASE-produced flakes. This thinning approach in combination with NASE can potentially produce MoS2 structure arrays with arbitrary thicknesses for meeting the requirements of various device applications.

Figure 13D:
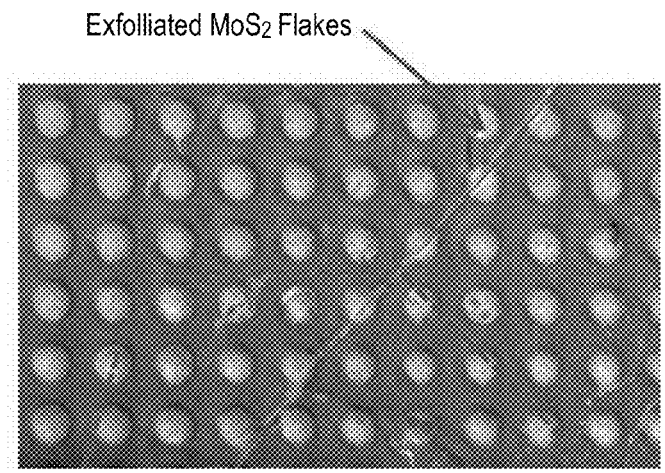
Figure 13E:
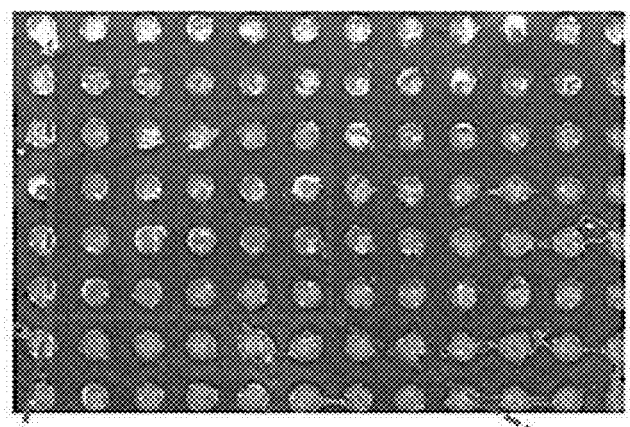
Figure 13E:
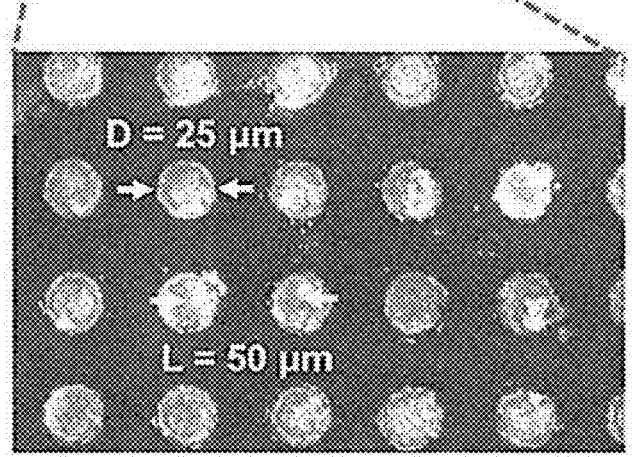

To study the effect of the lateral dimensions of MoS2 mesas on the quality of NASE-produced flake arrays, we also produced MoS2 flake arrays with different lateral dimensions. FIGS. 13C-13E display the SEM images of a set of NASE-produced arrays of multilayer MoS2 flakes with various flake diameters (D) and flake-to-flake spacings (L) (i.e., (d) D=7 µm, L=20 µm; (e) D=17 µm, L=30 µm; (f) D=25 µm, L=50 µm). For all of these samples, the imprint depth (dNIL) is ~50 nm. The flake arrays with D=7 and 17 µm exhibit very similar quality as compared to 15 µm size ones shown in FIG. 3 (a). Especially, most flakes in these arrays have relatively smooth top surfaces, as shown in FIGS. 13C and 13D. FIG. 13E shows that the NASE-produced array with D=25 µm also exhibits a comparable yield (~80%) of exfoliated MoS2 flakes, but the top surfaces of these 25 µm size flakes exhibit a noticeably larger roughness in comparison with those of the flakes with the smaller D values. This is attributed to the relatively low aspect-ratio (i.e., dNIL/D) of these 25 µm size flakes, which results in relatively low flake rigidity and therefore a high occurring probability of wrinkled MoS2 layers. In this disclosure, it was found that the quality of NASE-produced flakes is not sensitive to the flake spacing (L) or density. The relationship between the flake rigidity and the occurring probability of wrinkling in exfoliated layers is further discussed below based on molecular dynamics (MD) simulations.

Because NASE-produced MoS2 flakes are embedded into PS fixing layers, their thicknesses cannot be directly measured by using atomic force microscopy (AFM) or the color coding method.39 Especially, it should be noted that the MoS2 flakes, under OM illumination, exhibit varying colors ranging from green to deep blue, as demonstrated in FIG. 13A. Such a color variation among MoS2 flakes are mainly attributed to the spatial variation of the PS film thickness or the residual layer thickness (RLT), which are caused by the nonflatness of our current MoS2 stamps (or current commercially available MoS2 ingots). Therefore, such a color variation does not correctly indicate the thickness distribution among exfoliated MoS2 flakes. To evaluate the uniformity of NASE-produced MoS2 flake thicknesses, an AFM was employed to measure the effective well depth (dW) of imprinted PS wells bearing exfoliated MoS2 layers, as illustrated in FIG. 14A. The dW value of a MoS2-embedded well is assumed to be the difference between the imprint depth (dNIL, or the initial height of MoS2 mesas pre-structured on the stamp) and the thickness (tMoS2) of the MoS2 flake embedded inside this well. A 3-D AFM image was taken of an exemplary NASE-produced MoS2 flake exfoliated into an imprinted PS well. The AFM scanline is re-plotted in FIG. 14B. The dW value of this MoS2-embedded well is measured from the topographic difference between the center of this MoS2 flake and a location outside the well, as indicated by the arrows in FIG. 14B. For this specific imprinted well, dW is measured to be ~0, indicating that tMoS2 ~dNIL=40 nm. FIG. 14C displays the statistics of dW/dNIL values measured from 100 imprinted wells bearing MoS2 flakes. These structures were produced in a single NASE process. FIG. 14C shows that the standard deviation of dW/dNIL data (or the relative thickness error of NASE-produced multilayer MoS2 flakes) is estimated to ~12%. This relative thickness error is much smaller than those of multilayer structures produced by previously reported exfoliation methods.

To evaluate the uniformity of the electronic properties of multilayer MoS2 flakes produced by NASE, back-gated field-effect transistor (FET) arrays were fabricated with NASE-produced MoS2 channels and obtained the statistical data of the transfer characteristics of multiple FETs. For all as-fabricated FETs, the channel width (W) and length (L) are 15 and 10 µm, respectively; the MoS2 channel thickness is around 20 nm; the back-gate dielectric consists of a 300 nm thick thermally grown SiO2 layer plus a residual PS layer. Here, the residual PS thickness (tresidual) under each MoS2 channel is estimated to be thinner than 5 nm by using tresidual=tPS−dNIL, in which tPS is the initial PS layer thickness before the NASE process.

FIGS. 15A-15D show the statistics of field-effect mobility (p), On/Off currents (ION is the IDS measured at VG=60 V; IOFF is the minimum value of IDS within the VG range of +60 V), subthreshold swing (SS), and threshold voltage (VT) data, which were extracted from the transfer characteristic curves of these fabricated FETs. Specifically, the mean values of µ, ION, IOFF, SS, and VT were statistically measured to be p=46+10 cm2/Vs, ION=24.0+5.0 µA (or, 1.60+0.33 µA per 1 µm channel width), IOFF=21+20 pA, SS=11.9+2.7 V/dec, and VT=28+8 V, respectively. First, it should be noted that the relatively large SS values of the FETs are attributed to the relatively thick back-gate dielectric (i.e., 300 nm SiO2) used here, and such SS values could be significantly reduced by using much thinner dielectrics. The IOFF data of the FETs exhibit a much larger relative standard deviation (~95%) as compared to other parameters, which is mainly attributed to the measurement precision (2-10 pA) of our semiconductor analyzer. The quantity VT could have zero or negative values, and therefore the relative standard deviation of VT data is meaningless for evaluating the uniformity of the FETs. Therefore, the relative standard deviations of µ, ION, and SS data were used for evaluating the uniformity. The relative standard deviations of these parameters range from 21% to 23%. This shows that even though the post-NASE FET fabrication process is yet to be optimized, the current FET arrays made from NASE-produced multilayer MoS2 flakes already exhibit a good uniformity in critical FET parameters. The observed variances in the performance parameters of the FETs are mainly attributed to several possible factors, including (1) the device-to-device variance in the residual PS layer thicknesses; (2) the NASE-introduced defects as discussed above; (3) the contaminants introduced during the post-NASE FET fabrication processes; (4) intrinsic nonuniformity of the material properties of initial MoS2 ingots (e.g., crystal orientations, domain size distributions, and intrinsic defects).

To evaluate the effect of the residual PS layers on the uniformity of the electronic properties of NASE-produced MoS2 flakes, another process was used to make MoS2 FETs free of the residual PS. To make such FETs, a SiO2-coated p+-Si substrate bearing NASE-produced MoS2 flakes was soaked in toluene for 1-2 hours. Until this step, the sample had not been subjected to any plasma etching. Therefore, the imprinted PS on the substrate (including the residual PS layers under MoS2 flakes) was able to be completely removed because there is no crosslinking in PS. However, this cleaning process displaced (and even peeled) many MoS2 flakes and only a few survived MoS2 flakes were chosen for making FETs. Because the selected MoS2 flakes had been shifted away from their original array configurations, repetitive lithography, metal deposition, and lift-off processes were performed to make multiple FETs. In particular, special finger contacts (5 nm Ti/50 nm Au) were fabricated to access to individual selected MoS2 flakes. This was a time-consuming task and resulted in a much lower device yield as compared to the method, discussed above, for making FET arrays with the residual PS. Figure S2 in the supporting information displays two representative back-gated FETs made from multilayer MoS2 flakes that were cleaned by Toluene.

Device characterization shows that the field-effect mobility data measured from the PS-retained FETs (i.e., µ=46+10 cm2/Vs) have a slightly smaller mean value and a slightly larger standard deviation in comparison with those measured from the PS-free FETs (i.e., µ=53+7 cm2/Vs). This slight difference is attributed to the roughness scattering at the MoS2/PS interface, which could slightly reduce the field effect mobility of the multilayer MoS2 FET and broaden the dispersion of the mobility values measured from different FETs. Because such a PS-induced mobility reduction is estimated to be only ~13%, one can think that the presence of residual PS between multilayer MoS2 flakes and SiO2 gate dielectrics does not result in a detrimental damage to the mobility property of multilayer MoS2 FETs. In comparison with the PS-retained FETs, the PS-free FETs exhibit a smaller average SS (i.e., SS=8.4+1.1 V/dec for PS-free FETs, whereas SS=11.9+2.7 V/dec for PS-retained ones). This difference is attributed to that the residual PS layer under a MoS2 FET channel introduces an additional capacitor connected with the SiO2 capacitor in series, which decreases the overall gate dielectric capacitance and therefore increases the SS value of this FET. In addition, the relative standard deviation of the SS data measured from PS-retained FETs (~23%) is noticeably larger than that measured from PS-free FETs (~13%). This is attributed to the nonuniformity of the residual PS layer thicknesses under NASE-produced MoS2 flakes, which may introduce an additional nonuniformity in back-gate capacitances and hence the SS data of PS-retained FETs. In comparison with PS-free FETs, the PS-retained FETs have statistically more positive VT values (i.e., VT=−27+10 V for PS-free FETs, whereas VT=28+8 V for PS-retained ones). This difference is attributed to the polymer-induced surface-charge-transfer (SCT) doping (p-type doping) in MoS2 channels.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A biosensor, comprising:
   a substrate;
   a field effect transistor (FET) formed on the substrate, wherein the FET includes a channel comprised of a monolayer of transition metal dichalcogenides;
   an antibody functionalized onto an exposed top surface of the channel of the FET; and
   a reservoir layer deposited on top of the FET and enclosing the exposed top surface of the channel of the FET, wherein the reservoir layer forms a fluidic channel over top the exposed top surface of the channel of the FET and the fluidic channel has an inlet and an outlet.

2. The biosensor of claim 1 further comprises a pump fluidly coupled via a tube to the inlet of the fluidic channel and operable to drive an analyte of interest through the fluidic channel.

3. The biosensor of claim 2 further comprises a controller electrically connected to the FET, wherein the controller regulates conductance of the FET and measures transfer characteristics of the FET while an analyte of interest passes through the fluidic channel.

4. The biosensor of claim 2 further comprises a controller electrically connected to the FET, wherein the controller operates the FET in a subthreshold region and measures drain-to-source current of the FET while an analyte of interest passes through the fluidic channel.

5. The biosensor of claim 1 is fabricated using top-down lithographic techniques.

6. The biosensor of claim 1 wherein the monolayer of transition metal dichalcogenides is further defined as molybdenum disulfide or tungsten diselenide.

7. The biosensor of claim 1 wherein the reservoir layer is further defined as a silicone.

8. The biosensor of claim 1 wherein the analyte of interest is tumor necrosis factor alpha.

9. A biosensor, comprising:
   a substrate;
   a field effect transistor (FET) formed on the substrate, wherein the FET includes a channel comprised of a monolayer of transition metal dichalcogenides;
   an antibody functionalized onto an exposed surface of the channel of the FET;
   a reservoir layer deposited on top of the FET, wherein the reservoir layer forms a fluidic channel over top of the exposed surface of the channel of the FET and the fluidic channel having an inlet and an outlet, such that the fluidic channel does not pass through the channel of the FET and the top surface of the FET forms wall on bottom of the fluidic channel; and
   a pump fluidly coupled via a tube to the inlet of the fluidic channel.

10. The biosensor of claim 9 further comprises a controller electrically connected to the FET, wherein the controller regulates conductance of the FET and measures transfer characteristics of the FET while an analyte of interest passes through the fluidic channel.

11. The biosensor of claim 9 further comprises a controller electrically connected to the FET, wherein the controller operates the FET in a subthreshold region and measures drain-to-source current of the FET while an analyte of interest passes through the fluidic channel.

12. The biosensor of claim 9 is fabricated using top-down lithographic techniques.

13. The biosensor of claim 9 wherein the monolayer of transition metal dichalcogenides is further defined as molybdenum disulfide or tungsten diselenide.

14. The biosensor of claim 9 wherein the reservoir layer is further defined as a silicone.

15. The biosensor of claim 9 wherein the analyte of interest is tumor necrosis factor alpha.

* * * * *